US007235662B2

(12) United States Patent
Hadida-Ruah et al.

(10) Patent No.: US 7,235,662 B2
(45) Date of Patent: Jun. 26, 2007

(54) MODULATORS OF THE GLUCOCORTICOID RECEPTOR AND METHOD

(75) Inventors: Sara Sabine Hadida-Ruah, San Diego, CA (US); Xiaohui He, San Diego, CA (US); Johnny Yasuo Nagasawa, San Diego, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 335 days.

(21) Appl. No.: 10/865,444

(22) Filed: Jun. 10, 2004

(65) Prior Publication Data

US 2004/0266758 A1 Dec. 30, 2004

Related U.S. Application Data

(60) Provisional application No. 60/477,574, filed on Jun. 11, 2003.

(51) Int. Cl.
*C07D 241/36* (2006.01)
(52) U.S. Cl. ...................................... 544/343
(58) Field of Classification Search ...................... None
See application file for complete search history.

(56) References Cited

U.S. PATENT DOCUMENTS

| | | | | |
|---|---|---|---|---|
| 5,688,808 | A | 11/1997 | Jones et al. | 514/285 |
| 5,688,810 | A | 11/1997 | Jones et al. | 514/311 |
| 5,693,646 | A | 12/1997 | Jones et al. | 514/285 |
| 5,693,647 | A | 12/1997 | Jones et al. | 514/285 |
| 5,696,127 | A | 12/1997 | Jones et al. | 514/285 |
| 5,696,130 | A | 12/1997 | Jones et al. | 514/291 |
| 5,696,133 | A | 12/1997 | Jones et al. | 514/314 |
| 6,166,013 | A | 12/2000 | Coghlan et al. | 514/239.5 |
| 6,358,947 | B1 | 3/2002 | Zhi et al. | 514/229.5 |
| 6,380,207 | B2 | 4/2002 | Coghlan et al. | 514/285 |
| 6,436,985 | B2 | 8/2002 | Pinto | 514/439 |
| 2001/0041802 | A1 | 11/2001 | Kym et al. | 549/388 |
| 2001/0049377 | A1 | 12/2001 | Coghlan et al. | 514/285 |

FOREIGN PATENT DOCUMENTS

| | | |
|---|---|---|
| WO | WO 99/41256 | 8/1999 |
| WO | WO 01/16128 | 3/2001 |
| WO | WO 02/02565 | 1/2002 |

OTHER PUBLICATIONS

Al-Dabbagh and Smith, "Species differences in oxidative drug metabolism: some basic considerations," Archives of toxicology. Supplement. Archiv fur Toxikologie. supplement, vol. 7, pp. 219-231 (1984).*
Hans Bundgaard, Design of Prodrugs, p. 1, © 1985 Elsevier Science Publishers.*
Richard B. Silverman, The Organic Chemistry of Drug Design and Drug Action, pp. 352-400. © 1992 Academic Press, Inc.*
Vippagunta et al, "Crystalline Solids" Advanced Drug Delivery Reviews, vol. 48, pp. 3-26 (2001).*

Gavezzotti, "Are Crystal Structures Predictable?" Accounts of Chemical Research, vol. 27, pp. 309-314 (1994).*
Reichardt et al, "Repression of inflammatory responses in the absence of DNA binding by the glucocorticoid receptor" The EMBO Journal, vol. 20(24), pp. 7168-7173 (2001).*
Reichardt et al, "DNA Binding of the Glucocorticoid Receptor Is Not Essential for Survival" Cell, vol. 93, pp. 531-541 (1998).*
Baldwin, Jr., A.S., "The transcription factor NF-κB and human disease", The Journal of Clinical Investigation, vol. 107, No. 1, pp. 3-6 (2001).
Bamberger, C.M. et al., "Glucocorticoid Receptor β, a Potential Endogenous Inhibitor of Glucocorticoid Action in Humans", The Journal of Clinical Investigation, vol. 95, pp. 2435-2441 (1995).
Brandon, D.D. et al., "Genetic variation of the glucocorticoid receptor from a steroid-resistant primate", Journal of Molecular Endocrinology, vol. 7, pp. 89-96 (1991).
Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role CBP/P300 in nuclear receptor signaling", Nature, vol. 383, pp. 99-103 (1996).
Danielsen, M. et al., "The mouse glucocorticoid receptor: mapping of functional domains by cloning, sequencing and expression of wild-type and mutant receptor proteins", The EMBO Journal, vol. 5, No. 10, pp. 2513-2522 (1986).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Hollenberg, S.M. et al., "Primary structure and expression of a functional human glucocorticoid receptor cDNA", Nature, vol. 318, pp. 635-641 (1985).

(Continued)

*Primary Examiner*—Zachary C. Tucker
(74) *Attorney, Agent, or Firm*—Laurelee A. Duncan

(57) ABSTRACT

Novel non-steroidal compounds are provided which are glucocorticoid receptor modulators which are useful in treating diseases requiring glucocorticoid receptor agonist or antagonist therapy such as obesity, diabetes, inflammatory and immune disorders, and have the structure

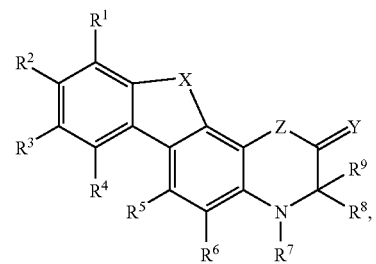

where $R^1$–$R^9$, X, Y and Z are defined herein.

18 Claims, No Drawings-

OTHER PUBLICATIONS

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Laudet, V. et al., The Nuclear Receptor FactsBook, Academic Press, publ., p. 345 (2002).

Miesfeld, R. et al., "Characterization of a steroid hormone receptor gene and mRNA in wild-type and mutant cells," Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor Is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 24, No. 24, pp. 7168-7173 (2001).

Stöcklin, E. et al., "Functional interactions between Stat5 and the glucocorticoid receptor", Nature, vol. 383, pp. 726-728 (1996).

Weinberger, C. et al., "Domain structure of human glucocorticoid receptor and its relationship to the v-*erb*-A oncogene product", Nature, vol. 318, pp. 670-672 (1985).

Weinberger, C. et al., "Identification of Human Glucocorticoid Receptor Complementary DNA Clones by Epitope Selction", Science, vol. 228, pp. 740-742 (1985).

Yang, K. et al., "Characterization of an ovine glucocorticoid receptor cDNA and developmental changes in its mRNA levels in the fetal sheep hypothalamus, pituitary gland and adrenal", Journal of Molecular Endocrinology, vol. 8, pp. 173-180 (1992).

Yang-Yen, H.-F. et al., "Transcriptional Interference between c-Jun and the Glucocorticoid Receptor: Mutual inhibition of DNA Binding Due to Direct Protein—Protein Interaction", Cell, vol. 62, pp. 1205-1215 (1990).

Zhi, L. et al., "5-Aryl-1,2,3,4-tetrahydrochromeno[3,4-*f*]quinolin-3-ones as a Novel Class of Nonsteroidal Progesterone Receptor Agonists: Effect of A-Ring Modification", J. Med. Chem., vol. 42, No. 8, pp. 1466-1472 (1999).

* cited by examiner

MODULATORS OF THE GLUCOCORTICOID RECEPTOR AND METHOD

This application claims priority to U.S. Provisional Application 60/477,574 filed Jun. 11, 2003, the entirety of which is incorporated herein by reference.

FIELD OF THE INVENTION

The present invention relates to new non-steroidal compounds which are glucocorticoid receptor (GR) modulators (that is agonists and antagonists) and thus are useful in treating diseases requiring glucocorticoid receptor agonist or antagonist therapy such as obesity, diabetes and inflammatory or immune associated diseases, and to a method for using such compounds to treat these and related diseases.

BACKGROUND OF THE INVENTION

The nuclear hormone receptor (NHR) family of transcription factors bind low molecular weight ligands and either stimulates or represses transcription. See, e.g., V. LAUDET ET AL., THE NUCLEAR RECEPTOR FACTS BOOK, 345, (2002). NHRs stimulate transcription by binding to DNA and inducing transcription of specific genes. NHRs may also stimulate transcription by not binding to DNA itself, rather they may modulate the activity of other DNA binding proteins. Stocklin, E., et al., *Nature* 383:726–8 (1996). The process of stimulation of transcription is called transactivation. NHRs repress transcription by interacting with other transcription factors or coactivators and inhibiting the ability of these other transcription factors or coactivators from inducing transcription of specific genes. This repression is called transrepression. For a review of this topic, see generally V. Laudet, supra, beginning at 42.

The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger, et al., *Science* 228, 640–742, (1985); Weinberger, et al., *Nature*, 318, 670–672 (1986) and for results in rats see Miesfeld, R., *Nature*, 312, 779–781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-kappaB and AP-1. This inhibition is termed transrepression. It has been shown that the primary mechanism for inhibition of these transcription factors by GR is via a direct physical interaction. This interaction alters the transcription factor complex and inhibits the ability of NF-kappaB and AP-1 to stimulate transcription. See Jonat, C., et al., *Cell*, 62, 1189 (1990); Yang-Yen, H. F., et al,. *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of coactivators by GR have also been proposed. See Kamer Y, et al., *Cell*, 85, 403 (1996); and Chakravarti, D. et al., *Nature*, 383, 99 (1996). NF-kappaB and AP-1 play key roles in the initiation and perpetuation of inflammatory and immunological disorders. See Baldwin, A S, *Journal of Clin. Investigation*, 107, 3 (2001); Firestein, G. S., and Manning, A. M., *Arthritis and Rheumatism*, 42, 609 (1999); and Peltz, G., *Curr. Opin, in Biotech.* 8, 467 (1997). NF-kappaB and AP-1 are involved in regulating the expression of a number of important inflammatory and immunomodulatory genes including: TNF-alpha, IL-1, IL-2, IL-5, adhesion molecules (such as E-selectin), chemokines (such as Eoxtaxin and Rantes), Cox-2, and others.

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell*, 93, 531 (1998) and Reichardt, H M, *EMBO J.*, 20, 7168 (2001).

The art is in need of modulators of NHRs. A modulator of an NHR may be useful in treating NHR-associated diseases, that is diseases associated with the expression products of genes whose transcription is stimulated or repressed by NHRs. For instance, the art is in need of modulators of NHRs that inhibit AP-1 and NFκB, as such compounds would be useful in the treatment of inflammatory and immune diseases and disorders such as osteoarthritis, rheumatoid arthritis, multiple sclerosis, asthma, inflammatory bowel disease, transplant rejection and graft vs. host disease.

Particularly concerning GR, although glucocorticoids are potent anti-inflammatory agents, their systemic use is limited by side effects. A compound that retained the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

SUMMARY OF THE INVENTION

In accordance with the present invention, compounds are provided having formula (I)

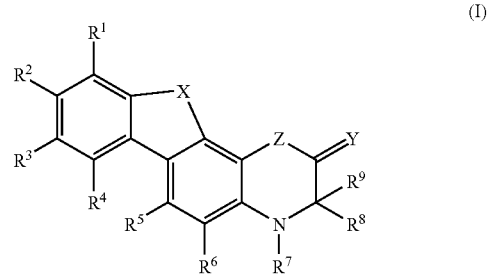

including all stereoisomers, salts, solvates or prodrugs thereof, wherein:

R¹ through R⁶ are independently
  (i) hydrogen, F, Cl, Br, I, NO₂, CN, OR¹⁰, NR¹⁰R¹¹, SR¹⁰, COR¹², CO₂R¹², or CONR¹⁰R¹¹; or
  (ii) C$_{1-6}$alkyl, C$_{3-8}$cycloalkyl, C$_{2-6}$alkenyl, C$_{2-6}$alkynyl, aryl or heteroaryl, each group of which is optionally substituted where valence allows by one or more groups, T¹, T² and/or T³;

Y is O, S or NR¹⁴;

Z is O, S, S(O), S(O)₂ or NR¹⁵;

X is OCR¹⁶R¹⁷, SCR¹⁶R¹⁷, S(O)CR¹⁶R¹⁷, S(O)₂CR¹⁶R¹⁷ NR¹⁴CR¹⁶R¹⁷, OC(O), SC(O), NR¹⁸C(O), CR¹⁶R¹⁷O, CR¹⁶R¹⁷S, CR¹⁶R¹⁷S(O), CR¹⁶R¹⁷S(O)₂ CR¹⁶R¹⁷NR¹⁴, C(O)O, C(O)S or C(O)NR¹⁸;

R⁷ and R¹⁵ are independently hydrogen, C$_{1-6}$alkyl, C$_{3-8}$cycloalkyl, C$_{1-6}$ haloalkyl, aryl, arylalkyl, heteroaryl, heteroarylalkyl, COR¹², CO₂R¹², SO₂R¹², S(O)R¹² or CONR¹⁰R¹¹;

R⁸ and R⁹ are independently hydrogen, C$_{1-6}$alkyl, C$_{3-8}$cycloalkyl, C$_{2-6}$alkenyl, C$_{2-6}$alkynyl, allyl, arylalkyl, aryl or heteroaryl, each group of which is optionally substituted where valence allows by one or more groups, T⁴, T⁵ and/or T⁶;

R¹⁰, R¹¹ and R¹⁴ are independently
  (i) hydrogen, C$_{1-6}$alkyl, C$_{3-8}$cycloalkyl, aryl, heteroaryl, each group of which is optionally substituted where valence allows, by one or more groups, T⁷, T⁸ and/or T⁹; or
  (ii) COR¹³, SO₂R¹³ or S(O)R¹³;

R¹² and R¹³ are independently hydrogen, C$_{1-6}$alkyl, C$_{3-8}$cycloalkyl, substituted C$_{1-6}$alkyl, haloalkyl, aryl, or heteroaryl, R¹⁶, R¹⁷ and R¹⁸ are independently hydrogen, C$_{1-6}$alkyl, C$_{3-8}$cycloalkyl, C$_{2-6}$alkenyl, C$_{2-6}$alkynyl, aryl or heteroaryl, each group of which is optionally substituted where valence allows by one or more groups, T¹⁰, T¹¹ and/or T¹²;

T¹–T¹² are each independently
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, each group of which is optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT¹³, —ST¹³, —C(O)$_t$H, —C(O)$_t$T¹³, —O—C(O)T¹³, -T²⁰C(O)$_t$N(T¹⁴)T¹³, —SO₃H, —S(O)$_t$T¹³, S(O)$_t$N(T¹⁴)T¹³, -T¹⁵-NT¹⁷T¹⁸, -T¹⁵-N(T¹⁴)-T¹⁶-NT¹⁷T¹⁸, -T¹⁵-N(T¹⁹)-T¹⁸-T¹³ and -T¹⁵-N(T¹⁹)-T¹⁶-H; or
  (ii) halo, cyano, nitro, OH, oxo, —SH, OT¹³, —ST¹³, —C(O)$_t$H, —C(O)$_t$T¹³, —O—C(O)T¹³, -T²⁰C(O)$_t$N(T¹⁴)T¹³, —SO₃H, —S(O)$_t$T¹³, S(O)$_t$N(T¹⁴)T¹³, -T¹⁵-NT¹⁷T¹⁸, -T¹⁵-N(T¹⁴)-T¹⁶-NT¹⁷T¹⁸, -T¹⁵-N(T¹⁹)-T¹⁸-T¹³ or -T¹⁵-N(T¹⁹)-T¹⁶-H;

t is 1 or 2;

T¹³ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T¹⁵ and T¹⁶ are each independently a single bond, -T²⁰-S(O)$_t$T²¹-, -T²⁰-C(O)-T²¹-, -T²⁰-C(S)-T²¹-, -T²⁰-O-T²¹-, -T²⁰-S-T²¹-, -T²⁰-O—C(O)-T²¹-, -T²⁰-C(O)$_t$T²¹-, -T²⁰-C(=NT²²)-T²¹- or -T²⁰-C(O)—C(O)-T²¹-;

T¹⁴, T¹⁷, T¹⁸, T¹⁹ and T²⁰ are independently alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT²³, —ST²³, —C(O)$_t$H, —C(O)$_t$T²³, —O—C(O)T²³, -T²⁰C(O)$_t$N(T²⁴)T²³, —SO₃H, —S(O)$_t$T²³, S(O)$_t$N(T²⁴)T²³, -T²⁵-NT²³T²⁴, -T²⁵-N(T²⁴)-T²⁶-NT²³T²⁴, -T²⁵-N(T²⁴)-T²⁶-T²³ and -T²⁵-N(T²⁴)-T²⁶—H; or T²¹ and T²² are each independently a single bond, alkylene, alkenylene or alkynylene;

T²³ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T²⁴ is hydrogen, halo, cyano, OH, —SH, oxo, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —C(O)$_t$H or —SO₃H; and T²⁵ and T²⁶ are each independently a single bond, —S(O)$_t$-, —C(O)—, —C(S)—, —O—, —S—, —O—C(O)—, —C(O)$_t$—, —C(=NT¹³)— or —C(O)—C(O)—.

In another aspect of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which includes a therapeutically effective amount (depending upon use) of a compound of formula (I) of the invention and a pharmaceutically acceptable carrier.

In still another aspect, the present invention provides a method of preventing, inhibiting onset of or treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, GR-associated diseases, that is a disease associated with the expression product of a gene whose transcription is stimulated or repressed by GR or a disease associated with GR transactivation, including inflammatory and immune diseases and disorders as described hereinafter, which includes the step of administering a therapeutically effective amount of a compound of formula (1) of the invention to a patient in need of treatment.

Another aspect of the present invention involves a method for preventing, inhibiting onset of or treating a disease associated with AP-1 and/or NFκB-dependent gene expression, that is a disease associated with the expression of a gene under the regulatory control of AP-1 and/or NFκB, such as inflammatory and immune disorders, cancer and tumor disorders, such as solid tumors, lymphomas and leukemia, and fungal infections such as mycosis fungoides.

DETAILED DESCRIPTION

The present invention relates to new non-steroidal compounds which are glucocorticoid receptor (GR) modulators (that is agonists and antagonists) and thus are useful in treating diseases requiring glucocorticoid receptor agonist or antagonist therapy such as obesity, diabetes and inflammatory or immune associated diseases, and to a method for using such compounds to treat these and related diseases.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition.

The terms "glucocorticoid receptor" and "GR," as used herein, refer either to a member of the nuclear hormone receptor family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. Science 228, p 640–742, 1985, and in Weinberger, et al. Nature, 318, p 670–672, 1986; rat glucocorticoid receptor as disclosed in Miesfeld, R. Nature, 312, p 779–781, 1985; mouse glucocortoid receptor as disclosed in Danielson, M. et al. EMBO J., 5, 2513; sheep glucocorticoid receptor as disclosed in Yang, K., et al. J. Mol. Endocrinol. 8, p 173–180, 1992; marmoset glucocortoid receptor as disclosed in Brandon, D. D., et al, J. Mol. Endocrinol. 7, p 89–96, 1991; and human GR-beta as disclosed in Hollenberg, S M. et al. Nature, 318, p 635, 1985, Bamberger, C. M. et al. J. Clin Invest. 95, p 2435, 1995.

The term, "disease associated with AP-1-dependent and/or NFκB -dependent gene expression," as used herein, refers to a disease associated with the expression product of a gene under the regulatory control of AP-1 and/or NFκB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); and inflammatory diseases such as osteoarthritis, acute pancreatitis, chronic pancreatitis, acute respiratory distress syndrome, Sezary's syndrome and vascular diseases which have an inflammatory and/or a proliferatory component such as restenosis, stenosis and artherosclerosis. Inflammatory or immune associated diseases or disorders also include, but are not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, and sepsis.

In addition, in accordance with the present invention a method of treating a disease associated with AP-1-induced and/or NFκB-induced transcription is provided wherein a compound of formula (I) of the invention is administered to a patient in need of treatment in a therapeutically effective amount to induce NHR transrepression of the AP-1-induced and/or NFκB-induced transcription, thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Preferred compounds include compounds within the scope of formula (I) (above), stereoisomers, salts, solvates or prodrugs thereof, in which Z is $NR^{15}$.

Other preferred compounds within the scope of formula (I) also includes compounds, stereoisomers, salts, solvates or prodrugs thereof, or a pharmaceutically acceptable salt thereof, in which X is $OCR^{16}R^{17}$, $SCR^{16}R^{17}$ or $NR^{14}CR^{16}R^{17}$.

Other preferred compounds within the scope of formula (I) include compounds, stereoisomers, salts, solvates or prodrugs thereof, in which $R^7$ is H or $C_{1-6}$alkyl.

Other preferred compounds within the scope of formula (I) are compounds, stereoisomers, salts, solvates or prodrugs thereof, in which Y is O or S.

Alternatively, preferred compounds are described by formula (II),

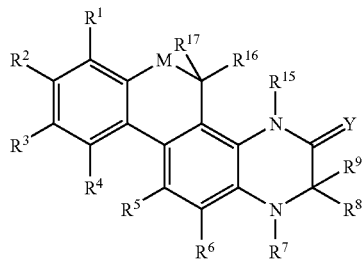

(II)

including all stereoisomers, salts, solvates or prodrugs thereof, wherein:

$R^1$ through $R^6$ are independently (i) hydrogen, F, Cl, Br, I, $NO_2$, CN, $OR^{10}$, $NR^{10}R^{11}$, $SR^{10}$, $COR^{12}$, $CO_2R^{12}$, $CONR^{10}R^{11}$; or (ii) $C_{1-6}$alkyl, $C_{3-8}$cycloalkyl, $C_{2-6}$alkenyl, $C_{2-6}$alkynyl, aryl or heteroaryl, each group of which is optionally substituted where valence allows by one or more groups, $T^1$, $T^2$ and/or $T^3$;

Y is O, S or $NR^{14}$;

M is O, S, S(O), or $S(O)_2$;

$R^7$ and $R^{15}$ are independently hydrogen, $C_{1-6}$alkyl, $C_{3-8}$cycloalkyl $C_{1-6}$haloalkyl, aryl, arylalkyl, heteroaryl, heteroarylalkyl, $COR^{12}$, $CO_2R^{12}$, $SO_2R^{12}$, $S(O)R^{12}$ or $CONR^{10}R^{11}$;

$R^8$ and $R^9$ are independently hydrogen, $C_{1-6}$alkyl, $C_{3-8}$cycloalkyl, $C_{2-6}$alkenyl, $C_{2-6}$alkynyl, allyl, arylalkyl, aryl or heteroaryl, each group of which is optionally substituted where valence allows by one or more groups, $T^4$, $T^5$ and/or $T^6$;

$R^{10}$, $R^{11}$ and $R^{14}$ are independently (i) hydrogen, $C_{1-6}$alkyl, $C_{3-8}$cycloalkyl, aryl or heteroaryl, each group of which is optionally substituted where valence allows, by one or more groups, $T^7$, $T^8$ and/or $T^9$; or (ii) $COR^{13}$, $SO_2R^{13}$ or $S(O)R^{13}$;

$R^{12}$ and $R^{13}$ are independently hydrogen, $C_{1-6}$alkyl, $C_{3-8}$cycloalkyl, substituted $C_{1-6}$alkyl, haloalkyl, aryl, or heteroaryl, $R^{16}$, $R^{17}$ and $R^{18}$ are independently hydrogen, $C_{1-6}$alkyl, $C_{3-8}$cycloalkyl, $C_{2-6}$alkenyl, $C_{2-6}$alkynyl, aryl or heteroaryl, each group of which is optionally substituted where valence allows by one or more groups, $T^{10}$, $T^{11}$ and/or $T^{12}$;

$T^1$–$T^{12}$ are each independently (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, each group of which is optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, $—OT^{13}$, $—ST^{13}$, $—C(O)_tH$, $—C(O)_tT^{13}$, $—O—C(O)T^{13}$, $-T^{20}C(O)_tN(T^{14})T^{13}$, $—SO_3H$, $—S(O)_tT^{13}$, $S(O)_tN(T^{14})T^{13}$, $-T^{15}-NT^{17}T^{18}$, $-T^{15}-N(T^{14})-T^{16}-NT^{17}T^{18}$, $-T^{15}-N(T^{19})-T^{18}-T^{13}$ and $-T^{15}-N(T^{19})-T^{16}-H$; or (ii) halo, cyano, nitro, OH, oxo, —SH, $OT^{13}$, $—ST^{13}$, $—C(O)_tH$, $—C(O)_tT^{13}$, $—O—C(O)T^{13}$, $-T^{20}C(O)_tN(T^{14})T^{13}$, $—SO_3H$, $—S(O)_tT^{13}$, $S(O)_tN(T^{14})T^{13}$, $-T^{15}-NT^{17}T^{18}$, $-T^{15}-N(T^{14})-T^{16}-NT^{17}T^{18}$, $-T^{15}-N(T^{19})-T^{18}-T^{13}$ or $-T^{15}-N(T^{19})-T^{16}H$;

t is 1 or 2;

$T^{13}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{15}$ and $T^{16}$ are each independently a single bond, $-T^{20}-S(O)_t-T^{21}-$, $-T^{20}-C(O)-T^{21}-$, $-T^{20}C(S)-T^{21}-$, $-T^{20}-O-T^{21}-$, $-T^{20}-S-T^{21}-$, $-T^{20}-O—C(O)-T^{21}-$, $-T^{20}-C(O)_tT^{21}-$, $-T^{20}-C(=NT^{22})-T^{21}-$ or $-T^{20}-C(O)—C(O)-T^{21}-$;

$T^{14}$, $T^{17}$, $T^{18}$, $T^{19}$ and $T^{20}$ are independently alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, $—OT^{23}$, $—ST^{23}$, $—C(O)_tH$, $—C(O)_tT^{23}$, $—O—C(O)T^{23}$, $-T^{20}C(O)_tN(T^{24})T^{23}$, $—SO_3H$, $—S(O)_tT^{23}$, $S(O)_tN(T^{24})T^{23}$, $-T^{25}-NT^{23}T^{24}$, $-T^{25}-N(T^{24})-T^{26}-NT^{23}T^{24}$, $-T^{25}-N(T^{24})-T^{26}-T^{23}$ and $-T^{25}-N(T^{24})-T^{26}-H$; or $T^{21}$ and $T^{22}$ are each independently a single bond, alkylene, alkenylene or alkynylene;

$T^{23}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{24}$ is hydrogen, halo, cyano, OH, —SH, oxo, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, $—C(O)_tH$ or $—SO_3H$; and $T^{25}$ and $T^{26}$ are each independently a single bond, $—S(O)_t—$, $—C(O)—$, $—C(S)—$, $—O—$, $—S—$, $—O—C(O)—$, $—C(O)_t—$, $—C(=NT^{13})-$ or $—C(O)—C(O)—$.

Preferred compounds, including all stereoisomers, salts, solvates or prodrugs thereof, within the scope of formula (II) include those compounds in which M is O or S, particularly those in which Y is O or S; even more particularly those in which $R^1$–$R^6$ are chosen independently from hydrogen, F, Cl, Br, I, $NO_2$, CN, $OR^{10}$, $NR^{10}R^{11}$, $SR^{10}$ and $C_{1-6}$alkyl optionally substituted by one or more groups, $T^1$, $T^2$ and/or $T^3$.

Especially preferred compounds, including all stereoisomers, salts, solvates or prodrugs thereof, within the scope of formula (II) are those in which $R^7$ and $R^{15}$ are independently H or $C_{1-6}$alkyl, and particularly those in which $R^8$, $R^9$, and $R^{17}$ are independently chosen from H and $C_{1-6}$alkyl.

Alternatively, preferred compounds are those within the scope of formula (II) having formula (III),

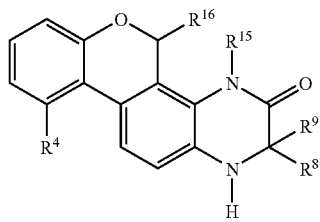

(III)

including all stereoisomers, salts, solvates or prodrugs thereof, wherein:

$R^4$ is $OR^{10}$ or $SR^{10}$; and $R^{10}$ is $C_{1-6}$alkyl optionally substituted where valence allows, by one or more groups, $T^7$, $T^8$ and/or $T^9$.

Particularly preferred compounds, including all stereoisomers, salts, solvates or prodrugs thereof, within the scope of formula (III) are those in which $R^4$ is $OC_{1-6}$alkyl; $R^8$ and $R^9$ are independently $C_{1-6}$alkyl; and $R^{16}$ is optionally substituted allyl (especially unsubstituted allyl) or optionally substituted aryl (especially unsubstituted aryl).

Alternatively, preferred compounds are those described by formula (IV),

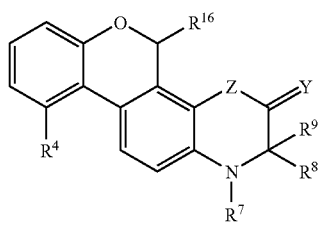

(IV)

including all stereoisomers, salts, solvates or prodrugs thereof, wherein:

$R^4$ is $OR^{10}$ or $SR^{10}$;

$R^7$ is hydrogen, $C_{1-6}$alkyl or $C_{1-6}$haloalkyl (especially hydrogen or $C_{1-6}$alkyl, more especially hydrogen);

$R^8$ and $R^9$ are independently chosen from H and $C_{1-6}$alkyl (especially $C_{1-6}$alkyl);

$R^{10}$ is $C_{1-6}$alkyl optionally substituted where valence allows, by one or more groups, $T^7$, $T^8$ and/or $T^9$;

Y is O, S or $NR^{14}$ (especially O);

Z is O, S, S(O), $S(O)_2$ or $NR^{15}$ (especially $NR^{15}$);

$R^{13}$ is hydrogen, $C_{1-6}$alkyl, $C_{3-8}$cycloalkyl, substituted $C_{1-6}$alkyl, haloalkyl, aryl or heteroaryl;

$R^{14}$ is hydrogen, $C_{1-6}$alkyl, $C_{3-8}$cycloalkyl or $C_{1-6}$alkyl by one or more groups, $T^7$, $T^8$ and/or $T^9$ (especially where $R^{14}$ is hydrogen or $C_{1-6}$alkyl);

$R^{15}$ is hydrogen, $C_{1-6}$alkyl, $C_{3-8}$cycloalkyl, $C_{1-6}$ haloalkyl, arylalkyl or heteroalkyl; and $R^{16}$ is hydrogen, $C_{1-6}$alkyl, $C_{3-8}$cycloalkyl, $C_{2-6}$alkenyl, $C_{2-6}$alkynyl, aryl or heteroaryl, each group of which is optionally substituted where valence allows by one or more groups, $T^{10}$, $T^{11}$ and/or $T^{12}$ (especially preferred $R^{12}$ is allyl or aryl, each group of which is optionally substituted by one or more groups, $T^{10}$, $T^{11}$ and/or $T^{12}$, more especially preferred is unsubstituted allyl or unsubstituted aryl).

Also preferred are compounds are selected from:

(i)

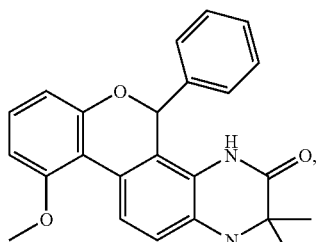

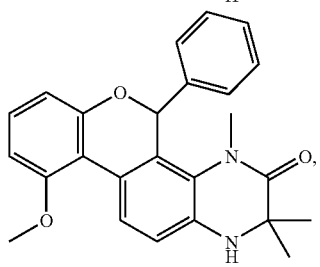

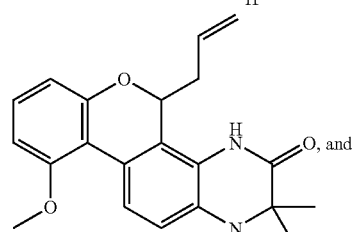

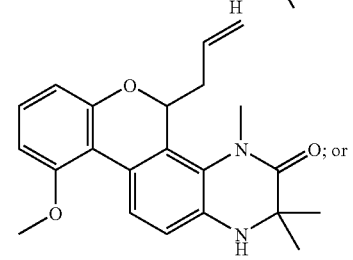

(ii) a stereoisomer, salt, solvate or prodrug, thereof.

Pharmaceutical compositions are those comprising a compound as defined in formulas (I), (II) or (III) as described above and a pharmaceutically acceptable carrier therefor.

Expecially preferred are pharmaceutical combinations comprising a compound as defined in (I), (II) or (III) as described above and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide;

the anti-obesity agent is a beta 3 adrenergic agonist, a lipase inhibitor, a serotonin (and dopamine) reuptake inhibitor, a thyroid receptor agonist, an aP2 inhibitor or an anorectic agent;

the lipid lowering agent is an MTP inhibitor, an HMG CoA reductase inhibitor, a squalene synthetase inhibitor, a fibric acid derivative, an upregulator of LDL receptor activity, a lipoxygenase inhibitor or an ACAT inhibitor; and the antihypertensive agent is an ACE inhibitor, angiotensin n receptor antagonist, NEP/ACE inhibitor, calcium channel blocker or β-adrenergic blocker.

Especially preferred combinations are those in particular wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, P32/98 and/or NVP-DPP-728A;

the anti-obesity agent is selected from orlistat, ATL-962, AJ9677, L750355, CP331648, sibutramine, topiramate, axokine, dexamphetamine, phentermine, phenylpropanolamine, and/or mazindol;

the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427;

the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440 or an angiotensin II receptor antagonist which is irbesartan, losartan or valsartan; amlodipine besylate, prazosin HCl, verapamil, nifedipine, nadolol, propranolol, carvedilol or clonidine HCl; and the platelet aggregation inhibitor is aspirin, clopidogrel, ticlopidine, dipyridamole or ifetroban.

Even more particularly preferred combinations are those wherein the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

In accordance with the present invention, preferred methods are provided for preventing or inhibiting the onset of or treating a GR-associated disease which is associated with the expression product of a gene whose transcription is stimulated or repressed by glucocorticoid receptors, which comprises administering to a patient in need of treatment a therapeutically effective amount of a compound having formulas (I), (II) or (III) as described above.

Preferred methods are those in which the GR-associated disease is an inflammatory or immune associated disease or disorder which is an endocrine disorder, rheumatic disorder, collagen disease, dermatologic disease, allergic disease, ophthalmic disease, respiratory disease, hematologic disease, gastrointestinal disease, inflammatory disease, autoimmune disease, neoplastic disease and metabolic disease.

Especially preferred are methods are those wherein the inflammatory or immune associated disease or disorder is transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, Type I and Type II diabetes, juvenile diabetes, obesity, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, viteligo, alopecia greata, autoimmune alopecia, autoimmune hypopituatarism, Guillain-Barre syndrome, and alveolitis; contact hypersensitivity, delayed-type hypersensitivity, contact dermatitis, uticaria, skin allergies, respiratory allergies, hayfever, allergic rhinitis and gluten-sensitive enteropathy, osteoarthritis, acute pancreatis, chronic pancreatitis, acute respiratory distress syndrome, Sezary's syndrome, restenosis, stenosis and artherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, psoriasis, seborrheic dermatitis, seasonal or perennial allergic rhinitis, bronchial asthma, contact dermatitis, atopic dermatitis, drug hypersensitivity reactions, allergic conjuncivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, Crohn's disease, Sjogren's syndrome, autoimmune vasculitis, multiple sclerosis, myasthenia gravis, sepsis and chronic obstructive pulmonary disease.

Also preferred are methods for preventing or inhibiting the onset of or treating a disease associated with AP-1 and/or NFκB induced transcription comprising administering to a patient in need of treatment a therapeutically effective amount of at least one compound having formulae (I) (II) or (II) as described above.

Also preferred are methods for preventing or inhibiting the onset of or treating a disease associated with AP-1 and/or NFκB dependent gene expression, that is a disease associated with the expression of a gene under the regulatory control of AP-1 and/or NFκB comprising administering to a patient in need of treatment a therapeutically effective amount of at least one compound having formulae (I) (II) or (III) as described above.

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given.

The synthesis of the desired tetracyclic lactone intermediates is described in Scheme I. Commercially available methyl 2-bromo-5-nitrobenzoate 1 is reduced to the corresponding aniline 2. The aniline 2 is then acetylated to obtain product 3. Nitration of the N-acetyl-protected aniline 3 yields nitrocompound 4 and its regio isomer. After isolating the desired product 4, the 1,2,3,4-tetrasubstituted benzene 5 is obtained by an acid-catalyzed deprotection of compound 4 with $BF_3 \cdot Et_2O$ in MeOH. Heating aniline 5 with neat 2-bromo-2-methyl-propionic acid methyl ester in the presence of KI and $Cs_2CO_3$ gives product 6. A Suzuki coupling of alkylated aniline 6, yields desired product 7 which is then reductively cyclized with $SnCl_2$ to give quinoxalinone 8. Finally, demethylation of 8 with in situ lactone formation gives the desired tetracyclic lactone intermediate.

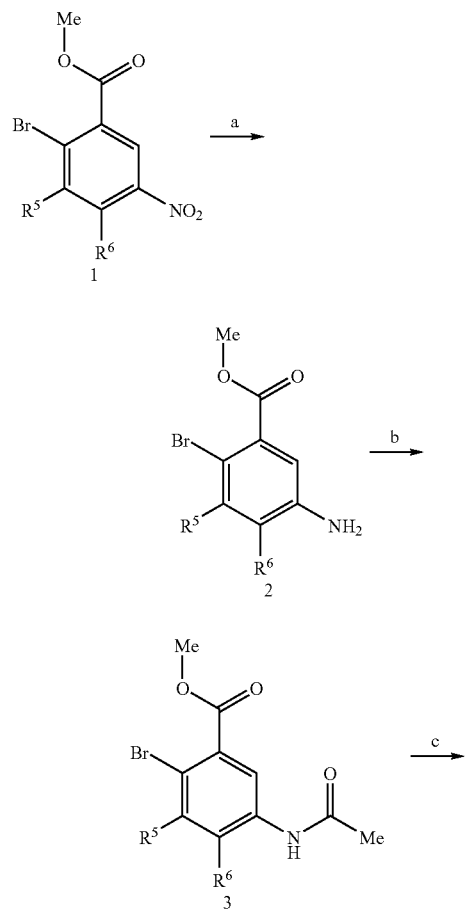

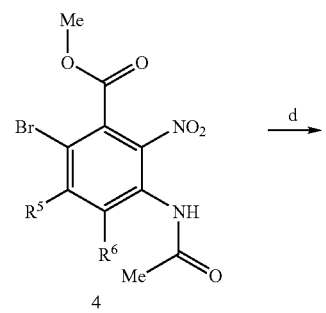

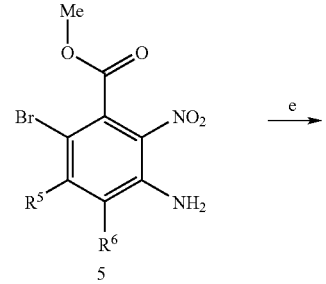

-continued

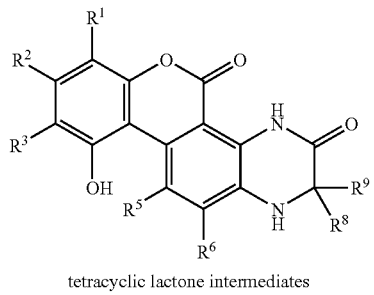

tetracyclic lactone intermediates a) SnCl$_2$, MeOH, reflux; b) AcCl, TEA, CH$_2$Cl$_2$, 0° C.; c) HNO$_3$, H$_2$SO$_4$, 0° C.;
d) BF$_3$•Et$_2$O, MeOH, reflux; e) bromo-2-methyl-propionic acid methyl ester, KI, Cs$_2$CO$_3$; f) see above; g) SnCl$_2$, MeOH, h) BBr$_3$, CH$_2$Cl$_2$, -78° C. to rt.

The preparation of the 5-aryl substituted analogs (A and B) is illustrated in Scheme II. The tetracyclic lactone intermediates are phenol re-methylated. At room temperature, the reaction provides predominantly the methoxy compound 9. At elevated temperature and in the presence of an excess of methyl iodide, both the phenol and the amide nitrogen are alkylated to provide 10. Subsequent nucleophilic addition of phenyl lithium to the C-5 carbonyl group of lactones 9 and 10 followed by dehydroxylation with Et$_3$SiH and BF$_3$•Et$_2$O gives the desired 5-aryl-substituted analogs, A and B, respectively.

Scheme 2

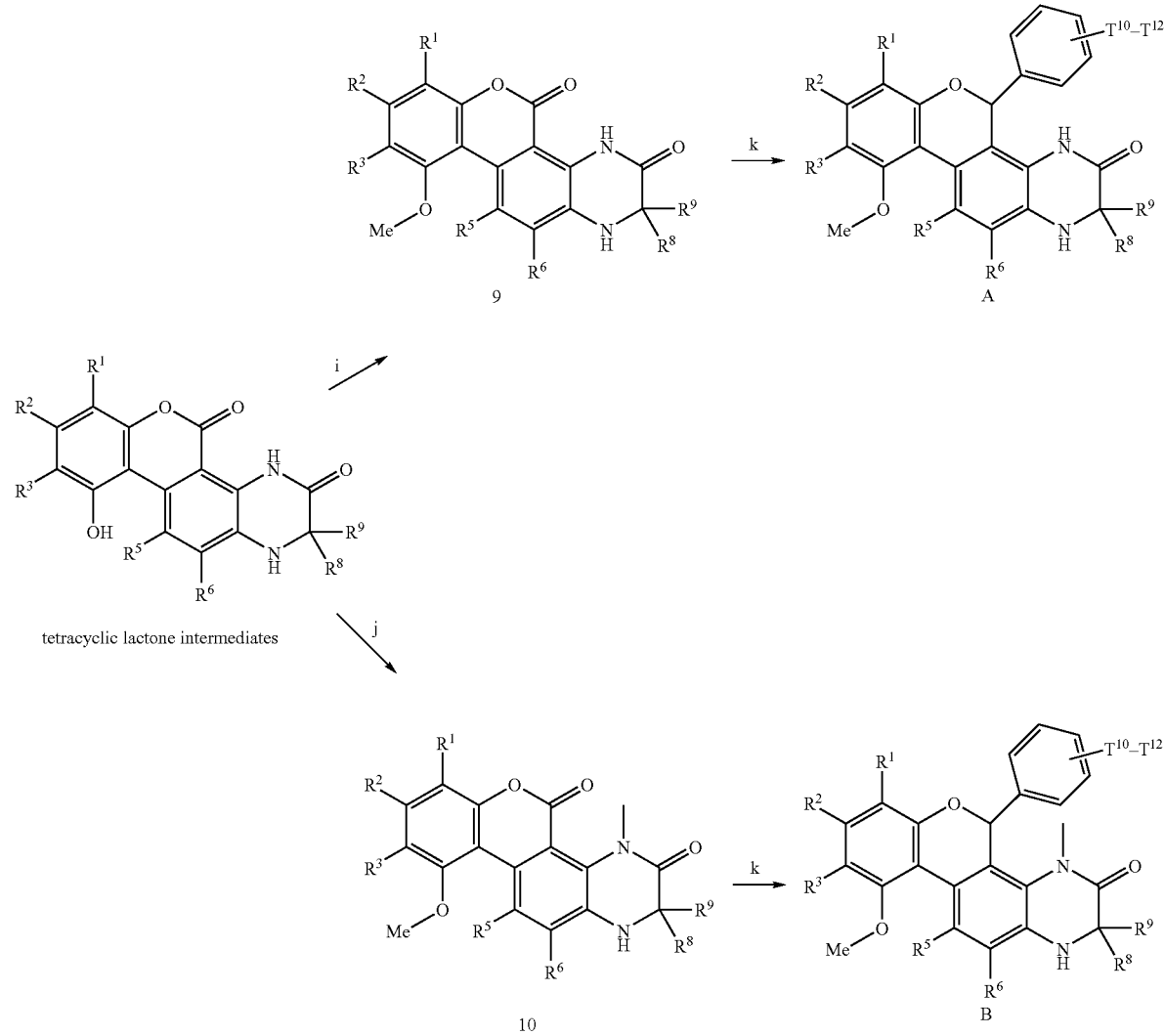

i) MeI, Cs$_2$CO$_3$, DMF, rt; j) MeI, Cs$_2$CO$_3$, DMF, 40° C., k) PhLi derivative, THF, -78° C., b) BF$_3$•Et$_2$O, Et$_3$SiH, CH$_2$Cl$_2$ The preparation of the 5-allyl substutited tetracyclic analogs is illustrated in Scheme 3. See Coghlan, M. J. et al., *J. Med Chem.*, 44, 2879–2885 (2001). The C-5 carbonyl of lactone 9 is reduced to the lactol 11. The corresponding methyl acetal 12 is then formed under acidic conditions. The C-5 methoxy group of 12 is then displaced with allyl magnesium bromide in the presence of $BF_3$ etherate to provide the desired 5-allyl-substituted tetracyclic compound C. Methylation of C provides the N-methyl substituted product D.

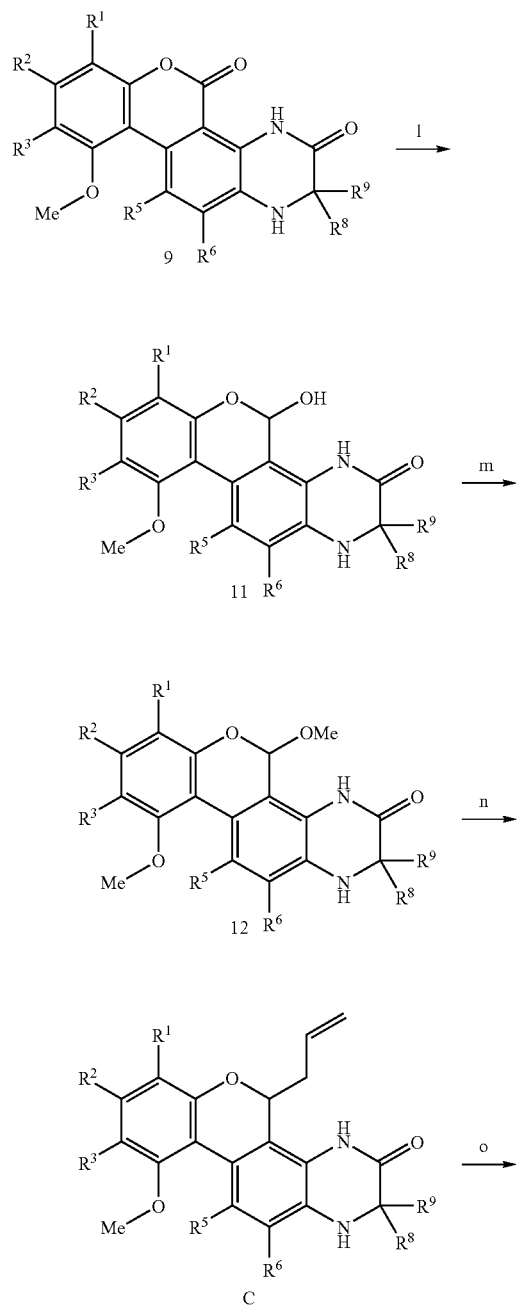

Scheme 3

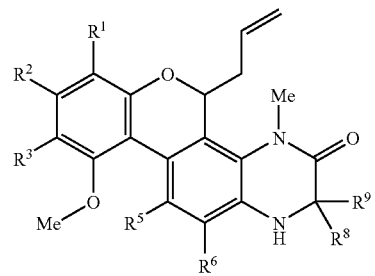

D l) LiAl(t-BuO)$_3$H, THF, 0° C. to rt; m) p-TSA, MeOH, 0° C. to rt; n) BF$_3$·Et$_2$O, CH$_2$=CHCH$_2$MgBr, Dichloroethane, -5° C.; o) MeI, Cs$_2$CO$_3$, CH$_3$CN, rt.

Definition of Terms

The following are definitions of terms used in this specification and appended claims. The initial definition provided for a group or term herein applies to that group or term throughout the specification and claims, individually or as part of another group, unless otherwise indicated.

The terms "alk" or "alkyl" refer to straight or branched chain hydrocarbon groups having 1 to 12 carbon atoms, preferably 1 to 8 carbon atoms. Lower alkyl groups, that is, alkyl groups of 1 to 6 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl groups substitued with one or more groups listed in the definition of $T^1$–$T^{12}$, preferably halo (e.g., trifluoromethyl), alkenyl, alkynyl, nitro, cyano, amino, oxo (=O), hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, —CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H —NH—CH(alkyl)-CO$_2$H, —NH—CH$_2$—CO$_2$-alkyl, —NH—CH(alkyl)-CO$_2$-alkyl, =N—OH, =N—O-alkyl, aryl, heteroaryl, heterocyclo, cycloalkyl, and substituted cycloalkyl, including phenyl, benzyl, phenylethyl, phenyloxy, and phenylthio. When a substituted alkyl includes an aryl, heterocyclo, or heteroaryl substituent, said ringed systems are as defined below and thus may have zero, one, two, or three substituents, listed in the definition of $T^1$–$T^{12}$.

When the term "alkyl" is used together with another group, such as in "arylalkyl", this conjunction defines with more specificity at least one of the substituents that the substituted alkyl will contain. For example, "arylalkyl"

refers to a substituted alkyl group as defined above where one of the substituents is aryl, such as benzyl.

The term heteroalkyl refers to straight or branched chain hydrocarbon groups, having single or double bonds, or combinations thereof, in which one or more skeletal atoms is oxygen, nitrogen, sulfur, or combinations thereof.

The term "alkenyl" refers to straight or branched chain hydrocarbon groups having 2 to 12 carbon atoms and at least one double bond. Alkenyl groups of 2 to 6 carbon atoms and having one double bond are preferred. A particularly preferred alkenyl group is an "allyl" group, defined herein as a 3 carbon hydrocarbon group having a double bond between the two carbons furthest from the point of attachment.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkoxy" refers to an alkyl or substituted alkyl group as defined above having one, two or three oxygen atoms (—O—) in the alkyl chain. For example, the term "alkoxy" includes the groups —O—$C_{1-12}$alkyl, —$C_{1-6}$alkylene-O—$C_{1-6}$alkyl, —$C_{1-4}$alkylene-O—$C_{1-4}$alkylene-O—$C_{1-6}$alkyl, O—$C_{1-4}$alkylene-O—$C_{1-4}$alkylene-O—$C_{1-4}$alkyl, and so forth.

The term "thioalkyl" or "alkylthio" refers to an alkyl or substituted alkyl group as defined above bonded through one or more sulfur (—S—) atoms. For example, the term "thioalkyl" or "alkylthio" includes the groups —S—$C_{1-2}$alkyl, —S—$C_{1-6}$alkylene-S—$C_{1-6}$alkyl, etc.

The term "aminoalkyl" refers to an alkyl or substituted alkyl group as defined above bonded through one or more nitrogen (—NR—) atoms. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—$NH_2$, —NH—$CH_3$, —$(CH_2)_2$—$NH_2$, —NH—$CH_2$—$CH_3$, —$CH_2$—$NH_2$—$CH_3$, and —N—$(CH_2)_2$. A lower aminoalkyl comprises an aminoalkyl having one to four carbon atoms. "Amino" refers to the group $NH_2$.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-2}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "acyl" refers to a carbonyl group

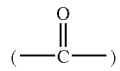

linked to an organic radical including an alkyl, alkenyl, alkynyl, aminoalkyl, substituted alkyl, substituted alkenyl, or substituted alkynyl, as defined above. The organic radical to which the carbonyl group is attached may be monovalent (e.g., —C(═O)-alkyl), or bivalent (e.g., —C(═O)alkylene, etc.)

The term "alkoxycarbonyl" refers to a carboxy or ester group

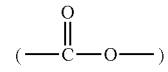

linked to an organic radical including an alkyl, alkenyl, alkynyl, aminoalkyl, substituted alkyl, substituted alkenyl, substituted alkynyl, or substituted aminoalkyl group, as defined above. The organic radical to which the carboxy group is attached may be monovalent (e.g., —$CO_2$-alkyl), or bivalent (e.g., —$CO_2$-alkylene, etc.)

The term "sulfonyl" refers to a sulphoxide group (i.e., —$S(O)_{1-2}$—) linked to an organic radical including an alkyl, alkenyl, alkynyl, aminoalkyl, substituted alkyl, substituted alkenyl, substituted alkynyl, or substituted aminoalkyl group, as defined above. The organic radical to which the sulphoxide group is attached may be monovalent (e.g., —$SO_2$-alkyl), or bivalent (e.g., —$SO_2$-alkylene, etc.)

The term "sulfonamide" refers to the group —$S(O)_2NR_aR_b$, wherein $R_a$ and $R_b$ may be hydrogen or alkyl, alkenyl, alkynyl, aminoalkyl, substituted alkyl, substituted alkenyl, substituted alkynyl, or substituted aminoalkyl group, as defined above. $R_a$ and $R_b$ may be monovalent or bivalent (e.g., —$SO_2$—NH-alkylene, etc.)

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents listed in the definition of $T^1$–$T^{12}$, preferably halo, alkyl, substituted alkyl (e.g., trifluoromethyl), alkenyl, alkynyl, nitro, cyano, amino, oxo, hydroxy, alkoxy, alkylthio, —NH(alkyl), —NH(cycloalkyl), —$N(alkyl)_2$, —$NHSO_2$, —$N(alkyl)SO_2$, —$NHSO_2$(alkyl), —$NHSO_2$(aryl), —N(alkyl)$SO_2$(alkyl), —N(alkyl)$SO_2$(aryl), —$SO_2$(alkyl), —$SO_2$(aryl), —$SO_2N$(aryl)(alkyl), —$SO_2N(alkyl)_2$, —$CO_2H$, —C(═O)H, $CO_2$-alkyl, —C(═O)alkyl, —C(═O)$NH_2$, —C(═O)NH(alkyl), —C(═O)NH(cycloalkyl), —C(═O)$N(alkyl)_2$, —NH—$CH_2$—$CO_2H$, —NH—CH(alkyl)-$CO_2H$, —NH—$CH_2$—$CO_2$-alkyl, —NH—CH(alkyl)-$CO_2$-alkyl, ═N—OH, ═N—O-alkyl, aryl, heteroaryl, heterocyclo, and a five or six membered ketal, e.g., 1,3-dioxolane or 1,3-dioxane.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl, with phenyl being preferred. The term "aryl" includes such rings having zero, one, two or three substituents listed in the definition of $T^1$–$T^{12}$, preferably halo, alkyl, substituted alkyl, alkenyl, alkynyl, nitro, cyano, amino, hydroxy, alkoxy, alkylthio, —NH(alkyl), —NH(cycloalkyl), —$N(alkyl)_2$, —$NHSO_2$, —$N(alkyl)SO_2$, —$NHSO_2$(alkyl), —$NHSO_2$(aryl), —N(alkyl)$SO_2$(alkyl), —N(alkyl)$SO_2$(aryl), —$SO_2$(alkyl), —$SO_2$(aryl), —$SO_2N$(aryl)(alkyl), —$SO_2N(alkyl)_2$, —$CO_2H$, —C(═O)H, $CO_2$-alkyl, —C(═O)alkyl, —C(═O)$NH_2$, —C(═O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, phenyl, benzyl, napthyl, phenylethyl, phenyloxy, phenylthio, cycloalkyl, substituted cycloalkyl, heterocyclo, and heteroaryl.

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents listed in the definition of $T^1$–$T^{12}$ preferably halo, alkyl, substituted alkyl, alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H, —NH—CH$_2$—CO$_2$-alkyl, —NHCH(C$_{1-4}$alkyl)-CO$_2$H, —NHCH(C$_{1-4}$alkyl)CO$_2$-alkyl, aryl, heteroaryl, heterocyclo, =N—OH, =N—O-alkyl, and a five or six membered ketal, e.g., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents listed in the definition of $T^1$–$T^{12}$ preferably halo, alkyl, substituted alkyl, alkenyl, alkynyl, nitro, cyano, amino, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, phenyl, benzyl, phenylethyl, phenyloxy, phenylthio, cycloalkyl, substituted cycloalkyl, heterocyclo, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "optionally substituted" is defined herein to be synonymous with substituted or unsubstituted.

$T^1$–$T^{12}$ are defined herein as follows and are each independently:

(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, each group of which is optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT$^{13}$, —ST$^{13}$, —C(O)$_t$H, —C(O)$_t$T$^{13}$, —O—C(O)T$^{13}$, -T$^{20}$C(O)$_t$N(T$^{14}$)T$^{13}$, —SO$_3$H, —S(O)$_t$T$^{13}$, S(O)$_t$N(T$^{14}$)T$^{13}$, -T$^{15}$-NT$^{17}$T$^{18}$, -T$^{15}$-N(T$^{14}$)-T$^{16}$-NT$^{17}$T$^{18}$, -T$^{15}$-N(T$^{19}$)-T$^{18}$-T$^{13}$ and -T$^{15}$-N(T$^{19}$)-T$^{16}$-H; or (ii) halo, cyano, nitro, OH, oxo, —SH, OT$^{13}$, —ST$^{13}$, —C(O)$_t$H, —C(O)$_t$T$^{13}$, —O—C(O)T$^{13}$, -T$^{20}$C(O)N(T$^{14}$)T$^{13}$, —SO$_3$H, —S(O)$_t$T$^{13}$, S(O)$_t$N(T$^{14}$)T$^{13}$, -T$^{15}$-NT$^{17}$T$^{18}$, -T$^{15}$-N(T$^{14}$)-T$^{16}$-NT$^{17}$T$^{18}$, -T$^{15}$-N(T$^{19}$)-T$^{18}$-T$^{13}$ or -T$^{15}$-N(T$^{19}$)-T$^{16}$-H;

t is 1 or 2;

$T^{13}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{15}$ and $T^{16}$ are each independently a single bond, -T$^{20}$-S(O)$_t$-T$^{21}$—, -T$^{20}$-C(O)-T$^{21}$-, -T$^{20}$-C(S)-T$^{21}$-, -T$^{20}$-O-T$^{21}$-, -T$^{20}$S-T$^{21}$-, -T$^{20}$-O—C(O)-T$^{21}$-, -T$^{20}$-C(O)$_t$T$^{21}$-, -T$^{20}$-C(=NT$^{22}$)-T$^{21}$- or -T$^{20}$-C(O)—C(O)-T$^{21}$-;

$T^{14}$, $T^{17}$, $T^{18}$, $T^{19}$ and $T^{20}$ are independently alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)

alkyl, cycloalkenyl, (cycloalkenyl)alkyl, aryl, (aryl)alkyl, heterocyclo, (heterocylco)alkyl, heteroaryl or (heteroaryl)alkyl, —OT, —ST, —C(O)$_t$H, —C(O)$_t$T$^{23}$, —O—C(O)T$^{23}$, -T$^{20}$C(O)$_t$N(T$^{24}$)T$^{23}$, —SO$_3$H, —S(O)$_t$T$^{23}$, S(O)$_t$N(T$^{24}$)T$^{23}$, T$^{25}$-NT$^{23}$T$^{24}$, -T$^{25}$-N(T$^{24}$)-T$^{26}$-NT$^{23}$T$^{24}$, -T$^{25}$-N(T$^{24}$)-T$^{26}$-T$^{23}$ and -T$^{25}$-N(T$^{24}$)-T$^{26}$-H; or T$^{21}$ and T$^{22}$ are each independently a single bond, alkylene, alkenylene or alkynylene;

T$^{23}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T$^{24}$ is hydrogen, halo, cyano, OH, —SH, oxo, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —C(O)$_t$H or —SO$_3$H; and T$^{25}$ and T$^{26}$ are each independently a single bond, —S(O)$_t$—, —C(O)—, —C(S)—, —O—, —S—, —O—C(O)—, —C(O)$_t$—, —C(=NT$^{13}$)- or —C(O)—C(O)—.

Throughout the specification, groups and substituents thereof may be chosen by one skilled in the field to provide stable moieties and compounds.

Compounds of Formula (I) include salts, prodrugs and solvates. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

For further examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, 8, 1–38 (1992), each of which is incorporated herein by reference.

Compounds of the formula (I), salts and prodrugs thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula (I) can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Combinations

Where desired, the compounds of formula (I) may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula (I) of the invention include cyclosporins, for example cyclosporin A, mycophenolate, interferon-beta, deoxyspergolin, FK-506 or Ant.-IL-2.

The anti-cancer agents which may be optionally employed in combination with compounds of formula (I) of the invention include azathiprine, 5-fluorouracil, cyclophosphamide, cisplatin, methotrexate, thiotepa, carboplatin, and the like.

The anti-viral agents which may be optionally employed in combination with compounds of formula (I) of the invention include abacavir, aciclovir, ganciclovir, zidanocin, vidarabine, and the like.

The anti-inflammatory agents which may be optionally employed in combination with compounds of formula (I) of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD 154, fusion proteins such as etanercept, fusion proteins constructed from CD40 and/or CD154gp39 (e.g. CD401g and CD8gp39), inhibitors, such as nuclear translocation inhibitors, of NF-kappa B function, such as deoxyspergualin (DSG).

The anti-fungal agents which may be optionally employed in combination with compounds of formula (I) of the invention include fluconazole, miconazole, amphotericin B, and the like.

The antibiotics which may be optionally employed in combination with compounds of formula (I) of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula (I) of the invention include methotrexate, leflunomide, FK506 (tacrolimus, Prograf), The hypolipidemic agent or lipid-lowering agent or lipid modulating agents which may be optionally employed in combination with the compounds of formula (I) of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712, 279, and 5,760,246.

The most preferred MTP inhibitor is 9-[4-[4-[[2-(2,2,2-Trifluoroethoxy)benzoyl]amino]-1-piperidinyl]butyl]-N-(2, 2,2-trifluoroethyl)-9H-fluorene-9-carboxamide

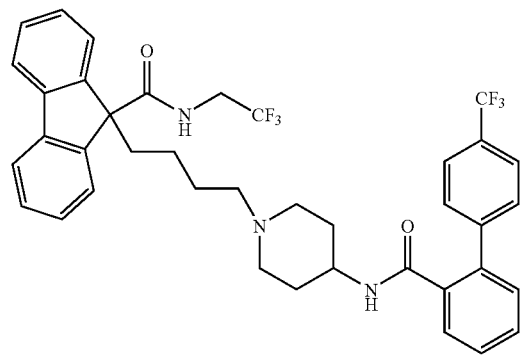

The hypolipidemic agent may be an HMG CoA reductase inhibitor which includes, but is not limited to, mevastatin and related compounds as disclosed in U.S. Pat. No. 3,983, 140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354, 772, cerivastatin disclosed in U.S. Pat. Nos. 5,006,530 and 5,177,080, atorvastatin disclosed in U.S. Pat. Nos. 4,681, 893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in Atherosclerosis 115, 45–63 (1995) and J. Med. Chem. 41, 973 (1998).

The hypolipidemic agent may be an ileal Na$^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD4522.

The above-mentioned U.S. patents are incorporated herein by reference. The amounts and dosages employed will be as indicated in the Physician's Desk Reference and/or in the patents set out above.

The compounds of formula (I) of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula (I) and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula (I) may be 1,2,3 or more antidiabetic agents or antihyperglycemic agents including insulin secretagogues or insulin sensitizers, or other antidiabetic agents preferably having a mechanism of action different from the compounds of formula (I) of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of formula (I) will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of formula (I) will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of formula (I) will be employed in a weight ratio to the glucosidase inhibitor within the range from about 0.01:1 to about 100:1, preferably from about 0.05:1 to about 10:1.

The compounds of formula (I) may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of formula (I) will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of formula (I).

The compounds of formula (I) may also be employed in combination with a antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an SGLT2 inhibitor such as disclosed in U.S. application Ser. No. 09/679,027, filed Oct. 4, 2000 (attorney file LA49 NP), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27 NP), employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula (I) of the invention may be repaglinide, nateglinide (Novartis) or KAD1229 (PF/Kissei), with repaglinide being preferred.

The compound of formula (I) will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula (I) may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula (I) may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula (I) may be orlistat or ATL-962 (Alizyme), with orlistat being preferred.

The serotonin (and dopoamine) reuptake inhibitor which may be optionally employed in combination with a compound of formula (I) may be sibutramine, topiramate (Johnson & Johnson) or axokine (Regeneron), with sibutramine and topiramate being preferred.

The thyroid receptor agonist which may be optionally employed in combination with a compound of formula (I) may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula (I) may be dexamphetamine, phentermine, phenylpropanolamine or mazindol, with dexamphetamine being preferred.

The various anti-obesity agents described above may be employed in the same dosage form with the compound of formula (I) or in different dosage forms, in dosages and regimens as generally known in the art or in the PDR.

The antihypertensive agents which may be employed in combination with the compound of formula (I) of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (-S-) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432, 971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5- tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R-31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]] 3R (*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula (I) include hydrochlorothiazide, torasemide, furosemide, spironolactono, and indapamide.

Antiplatelet agents which may be employed in combination with compounds of formula (I) of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula (I) of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compunds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrastemal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of formula (I) (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of formula (I) into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transscriptional assays.

The cellular transrespressional assay and cellular transcriptional assay employed to determine activity are described in copending provisional application No. 60/396,907, filed Jul. 18, 2002 which is incorporated herein by reference.

Glucocorticoid Receptor Binding Assay

In order to measure the binding of compounds to the glucocorticoid receptor a commercially available kit was used (Glucocorticoid receptor competitor assay kit, Panvera Co., Madison, Wis.). Briefly, a cell lysate containing the glucocorticoid receptor was mixed with a fluorescently labeled glucocorticoid (dexamethasone) plus or minus test molecule. After one hour at room temperature, the fluorescence polarization (FP) of the samples were measured. The FP of a mixture of receptor, fluorescent probe (i.e. fluorescently labeled glucocorticoid) and 1 mM dexamethasone represented 100% competition, whereas, the FP of the mixture without dexamethasone was taken to be 100% binding. The percentage competition of test molecules was then compared to the sample with 1 mM dexamethasone and expressed as % relative binding activity with dexamethasone being 100% and no competition being 0%. Test molecules were analyzed in the concentration range from 0.1 nM to 40 µM.

Other features of the invention will become apparent in the course of the following descriptions of exemplary embodiments that are given for illustration of the invention and are not intended to be limiting thereof.

EXAMPLES

The following abbreviations are employed in the Preparations and Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3N$=triethylamine
NMM=N-methyl morpholine
DMAP=4-dimethylaminopyridine
NaBH4=sodium borohydride
$NaBH(OAc)_3$=sodium triacetoxyborohydride
DIBALH=diisobutyl aluminum hydride
LAH or $LiAlH_4$=lithium aluminum hydride
n-BuLi=n-butyllithium
LDA=lithium diisopropylamide
Pd/C=palladium on carbon
$PtO_2$=platinum oxide
KOH=potassium hydroxide
NaOH=sodium hydroxide
LiOH=lithium hydroxide
$K_2CO_3$=potassium carbonate
$NaHCO_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
$NaN(TMS)_2$=sodium hexamethyldisilazide or sodium bis(trimethylsilyl)amide
$Ph_3P$=triphenylphosphine
$Pd(OAc)_2$=Palladium acetate
$(Ph_3P)_4Pd^0$=tetrakis triphenylphosphine palladium
DEAD=diethyl azodicarboxylate DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point Materials.

Reactions requiring air-sensitive manipulations were conducted under $N_2$ atmosphere. Analytical TLC was performed on 0.20 mm silica gel 60 F254 plates. Merck silica gel (60, particle size 0.040–0.063 mm) was used for flash column chromatography. NMR spectra were recorded on Varian Mercury 300 MHz spectrometers. Chemical shifts (δ) were measured in parts per million (ppm), and coupling constants (J values) are in Hz. High-resolution mass spectra (HR-MS) were recorded on a Micromass Q-TOF spectrometer. All chemicals were purchased from different commercial sources. Most of the reactions were carried out without optimization of the yield.

Preparations

The preparations set out below are for the synthesis of intermediates that were not obtained from commercial sources and were employed for the preparation of compounds of formula (I) of the invention. All chemical structures in the tables and schemes are racemic unless specified otherwise.

5-Amino-2-bromo-benzoic acid methyl ester (i)[13]

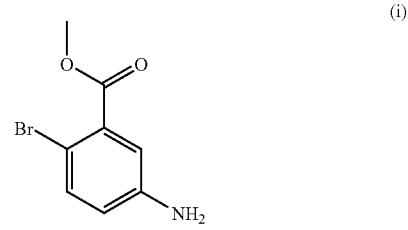

A solution containing 2-bromo-5-nitro-benzoic acid methyl ester (25.55 g, 98.26 mmol) and tin(II) chloride (93.25 g, 491.83 mmol) in MeOH (500 mL) was heated at reflux for 1.5 h. The solvent was removed under reduced pressure and EtOAc (500 mL) was added. The solution was neutralized with 4M solution of NaOH to pH=9. The resulting precipitate was filtered through celite. The organic layer was washed with saturated aqueous NaHCO$_3$ (3×200 mL), H$_2$O (1×200 mL), brine (1×200 mL), and dried (Na$_2$SO$_4$). The solvent was removed under reduced pressure to yield the desired product i as a yellow oil (20.89 g, 92%). $^1$H NMR (acetone-d$_6$): δ 7.25 (d, J=8.4 Hz, 1H), 7.00 (d, J=3.0 Hz, 1H), 6.67 (dd, J=8.4, 3.0 Hz, 1H), 4.99 (br s, 2H), 3.76 (s, 3H).

5-Acetylamino-2-bromo-benzoic acid methyl ester (ii)

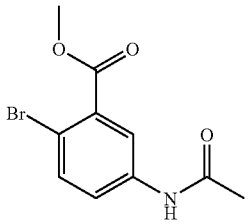

(ii)

To a solution of 5-amino-2-bromo-benzoic acid methyl ester (i) (20.89 g, 90.78 mmol) and triethylamine (19.0 mL, 136.30 mmol) in CH$_2$Cl$_2$ (450 mL) at 0° C. was added acetylchloride (13.0 mL, 182.83 mmol). The reaction mixture was stirred at 0° C. for 1 hour and warmed to room temperature. The mixture was then washed with H$_2$O (2×200 mL), saturated aqueous NaHCO$_3$ (2×200 mL), brine (1×200 mL), and dried with Na$_2$SO$_4$. The solvent was removed under reduced pressure to yield the desired product 14 as a white solid (21.31 g, 87%). $^1$H NMR (acetone-d$_6$): δ 9.31 (br s, 1H), 8.04 (d, J=2.7 Hz, 1H), 7.65 (dd, J=8.7, 2.7 Hz, 1H), 7.54 (d, J=2.7 Hz, 1H), 3.81 (s, 3H), 2.03 (s, 3H). Anal. Calcd for C$_{10}$H$_{10}$BrNO$_3$: C, 44.14; H, 3.70; N, 5.15. Found: C, 44.53; H, 3.57; N, 4.68.

3-Acetylamino-6-bromo-2-nitro-benzoic acid methyl ester (iii)

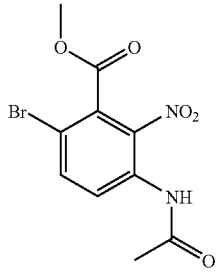

(iii)

To a solution of 5-acetylamino-2-bromo-benzoic acid methyl ester (ii, 5.44 g, 20.0 mmol) in H$_2$SO$_4$ (50 mL) at 0° C. was added HNO$_3$ (50 mL). The reaction mixture was stirred at 0° C. for 20 min and poured into ice water (200 mL). The mixture was then extracted with EtOAc (3×200 mL). The combined extracts were washed with saturated aqueous NaHCO$_3$ (3×200 mL), H$_2$O (3×200 mL), brine (1×200 mL), and dried with Na$_2$SO$_4$. Flash column chromatography gave the desired product iii as a yellow solid (3.60 g, 57%). $^1$H NMR (acetone-d$_6$): δ 9.47 (br s, 1H), 8.02 (d, J=9.0 Hz, 1H), 7.89 (d, J=9.0, 1H), 3.84 (s, 3H), 2.10 (s, 3H). Anal. Calcd for C$_{10}$H$_9$BrN$_2$O$_5$: C, 37.88; H, 2.86; N, 8.83. Found: C, 38.02; H, 2.74; N, 8.74.

3-Amino-6-bromo-2-nitro-benzoic acid methyl ester (iv)

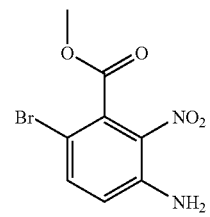

(iv)

A solution of 3-acetylamino-6-bromo-2-nitro-benzoic acid methyl ester (iii, 5.53 g, 17.42 mmol) and BF$_3$.Et$_2$O (10.0 mL, 78.91 mmol) in MeOH (100 mL) was heated to reflux for 2 h and cooled to room temperature. The reaction mixture was neutralized with solid NaHCO$_3$ and the solvent was removed under reduced pressure. The solid residu was dissolved in EtOAc (400 mL) and washed with H$_2$O (3×200 mL), brine (1×200 mL), and dried with Na$_2$SO$_4$. The solvent was removed under reduced pressure to yield the desired product iv as an orange solid (4.74 g, 100%). $^1$H NMR (CDCl$_3$): δ 7.40 (d, J=9.3 Hz, 1H), 6.70 (d, J=9.3 Hz, 1H), 6.09 (br s, 2H), 3.90 (s, 3H). Anal. Calcd for C$_8$H$_7$BrN$_2$O$_4$: C, 34.93; H, 2.57; N, 10.18. Found: C, 35.08; H, 2.49; N, 10.06.

6-Bromo-3-(1-methoxycarbonyl-1-methyl-ethylamino)-2-nitro-benzoic acid methyl ester (v)

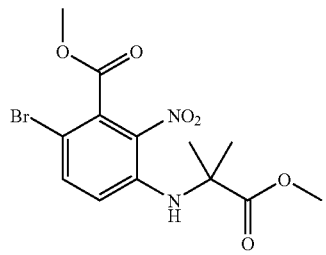

(v)

A solution of 3-amino-6-bromo-2-nitro-benzoic acid methyl ester (iv) (4.55 g, 16.54 mmol), methyl-bromoisobutyrate (21.0 mL, 162.29 mmol), cesium carbonate (21.94 g, 67.34 mmol), and potassium iodide (2.90 g, 17.44 mmol) was heated at 85° C. for 48 h and cooled to room temperature. The reaction mixture was partitioned between EtOAc (300 mL) and H$_2$O (300 mL). The organic layer was washed with H$_2$O (3×100 mL), brine and dried with Na$_2$SO$_4$. The solvents were removed under vacuum and the residue purified by flash column chromatography (silica gel, EtOAc/ hexane) to yield the desired product v as an orange solid (1.23 g, 20%). $^1$H NMR (CDCl$_3$): δ 8.22 (br s, 1H), 7.42 (d, J=9.0 Hz, 1H), 6.45 (d, J=9.0 Hz, 1H), 3.90 (s, 3H), 3.65 (s, 3H), 1.49 (s, 6H). Anal. Calcd for C$_{13}$H$_{15}$BrN$_2$O$_6$: C, 41.62; H, 4.03; N, 7.47. Found: C, 41.58; H, 3.93; N, 7.38.

2',6'-Dimethoxy-4-(1-methoxycarbonyl-1-methyl-ethylamino)-3-nitro-biphenyl-2-carboxylic acid methyl ester (vi)

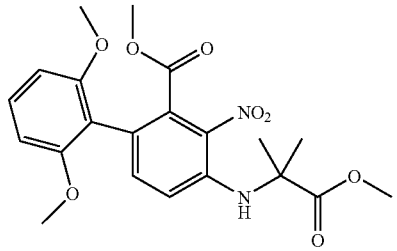

(vi)

Bromide v (1.05 g, 2.81 mmol), 2,6-dimethoxyphenylboronic acid (1.02 g, 5.62 mmol), cesium carbonate (2.74 g, 8.42 mmol), Pd(dppf) Cl$_2$∩CH$_2$Cl$_2$ (229 mg, 0.28 mmol) were added to DMF (20 mL). The mixture was degassed, filled with nitrogen and heated to 85° C. for 3 h. The mixture was then cooled to room temperature, poured into water (100 mL) and extracted with EtOAc (3×50 mL). The combined extracts were washed with brine and dried with MgSO$_4$. The solvent was removed under reduced pressure and the residue was purified by flash column chromatography (silica gel, EtOAc/hexane, 0% to 32%) to provide the product vi as an orange solid (860 mg, 71%). $^1$H NMR (CDCl$_3$) δ 7.39 (br, 1H), 7.22 (d, J=9 Hz, 1H), 7.21 (t, J=9 Hz, 1H), 6.74 (d, J=9 Hz, 1H), 6.60 (d, J=9 Hz, 2H), 3.67 (s, 3H), 3.61 (s, 6H), 3.42 (s, 3H), 1.62 (s, 6H). Anal. Calcd for C$_{21}$H$_{24}$N$_2$O$_8$·⅓H$_2$O: C, 57.53; H, 5.67; N, 6.39. Found: C, 57.64; H, 5.35; N, 6.02.

6-(2,6-Dimethoxy-phenyl)-2,2-dimethyl-3-oxo-1,2,3,4-tetrahydro-quinoxaline-5-carboxylic acid methyl ester (vii)

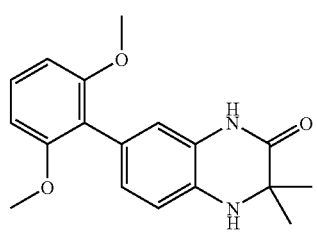

(vii)

To a solution of biphenyl vi (800 mg, 1.85 mmol) in EtOH (20 mL) was added tin(II) chloride (1.76 g, 9.26 mmol). The mixture was heated at reflux for 16 h and then cooled to room temperature. The reaction mixture was diluted with EtOAc (50 mL) and basified with saturated aqueous NaHCO$_3$. The resulting white suspension was stirred at room temperature for 30 min, then filtered through celite and the precipitate was washed by EtOAc (3×20 mL). The two layers were separated and the organic layer was collected. The aqueous layer was extracted with EtOAc (2×30 mL). The combined organic layers were washed with brine and dried over MgSO$_4$. After the solvent was removed under reduced pressure, the residue was purified by flash chromatography (EtOAc/hexane, 40% to 70%) to yield vii as a light yellow solid (500 mg, 73%). $^1$H NMR (CDCl$_3$): δ 7.93 (br s, 1H), 7.14 (t, J=8.4 Hz, 1H), 6.73 (m, 2H), 6.51 (d, J=8.4 Hz, 1H), 3.62 (s, 6H), 3.37 (s, 3H), 1.34 (s, 6H). Anal. Calcd for C$_{20}$H$_{22}$N$_2$O$_5$: C, 64.85; H, 5.99; N, 7.56. Found: C, 65.00; H, 5.73; N, 7.31.

10-Hydroxy-2,2-dimethyl-1,4-dihydro-2H-6-oxa-1,4-diaza-chrysene-3,5-dione (viii)

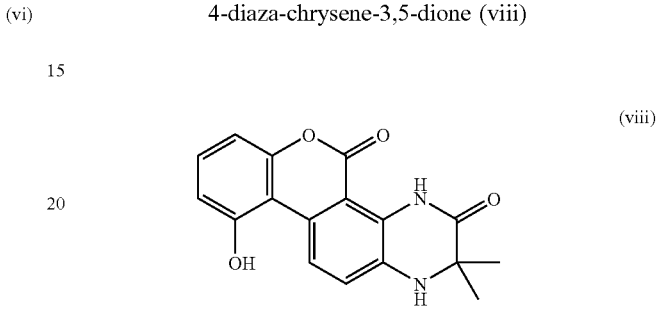

(viii)

Quinoxalinone vii (420 mg, 1.14 mmol) was dissolved in dry CH$_2$Cl$_2$ (10 mL) and cooled to −78° C. under an atmosphere of N$_2$. BBr$_3$ (536 μL, 5.68 mmol) was added dropwise. After the addition, the reaction mixture was warmed to room temperature and stirred for 2 h. The mixture was cooled to −78° C. and MeOH (3 mL) was added to quench the reaction. The mixture was concentrated under reduced pressure and then diluted with water (30 mL) and extracted with EtOAc (7×50 mL). The organic layers were combined and solvent was removed under reduced pressure to provide crude product (350 mg) as a yellow solid. A small portion of the crude material was purified by reverse phase preparative HPLC for characterization, the rest of the crude was used directly for the next step without any further purification. $^1$H NMR (CD$_3$OD) δ 8.74 (d, J=9 Hz, 1H), 7.14 (d, J=9 Hz, 1H), 7.13 (t, J=9 Hz, 1H), 6.74 (d, J=9 Hz, 1H), 6.72 (d, J=9 Hz, 1H), 1.33 (s, 6H). Anal. Calcd for C$_{17}$H$_{14}$N$_2$O$_4$ ⅙CF$_3$COOH: C, 63.22; H, 4.34; N, 8.51. Found: C, 63.54; H, 4.50; N, 8.32.

10-Methoxy-2,2-dimethyl-1,4-dihydro-2H-6-oxa-1,4-diaza-chrysene-3,5-dione (ix)

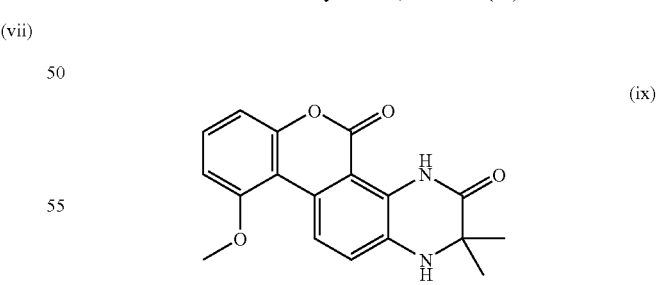

(ix)

To a solution of phenol viii (200 mg, 0.65 mmol) in DMF (10 mL) was added cesium carbonate (419 mg, 1.29 mmol) and methyl iodide (88 μL, 1.42 mmol). The mixture was stirred at room temperature for 1 h and then poured into cold water (50 mL). The mixture was then extracted with EtOAc (5×50 mL). The combined extracts were washed with brine and dried (MgSO$_4$). The solvent was removed under reduced pressure to provide the crude tetracyclic lactone ether ix (163 mg) as a yellow solid that was used in the next step without further purification. A small portion of the crude ix was purified by reverse phase preparative HPLC for characterization. $^1$H NMR (acetone-d$_6$) δ 10.90 (br s, 1H), 8.59 (d, J=8.4, 1H), 7.34 (t, J=8.4 Hz, 1H), 7.21 (d, J=8.4, 1H), 6.98 (d, J=8.4, 1H), 6.90 (d, J=8.4 Hz, 1H), 5.93 (br s, 1H), 4.01 (s, 3H), 1.34 (s, 6H). Anal. Calcd for C$_{18}$H$_{16}$N$_2$O$_4$: C, 66.66; H, 4.97; N, 8.64. Found: C, 66.66; H, 4.79; N, 8.96.

10-Methoxy-2,2,4-trimethyl-1,4-dihydro-2H-6-oxa-1,4-diaza-chrysene-3,5-dione (x)

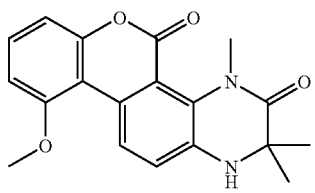

To a solution of tetracyclic lactone ix (100 mg, 0.32 mmol) in DMF (5 mL) was added cesium carbonate (263 mg, 0.81 mmol) and methyl iodide (100 μL, 1.60 mmol). The mixture was stirred at 40° C. overnight, poured into water (30 mL) and extracted with EtOAc(3×30 mL). The combined extracts were washed with brine and dried (MgSO$_4$), the solvent was removed under reduced pressure to yield a product that was used in the next step with no further purification. A small portion of the residue was purified by reverse phase preparative HPLC for characterization. $^1$H NMR (acetone-d$_6$) δ 8.69 (d, J=8.4 Hz, 1H), 7.39 (t, J=8.4 Hz, 1H), 7.31 (d, J=8.4, 1H), 7.02 (d, J=8.4, 1H), 6.94 (d, J=8.4 Hz, 1H), 6.04 (br, 1H), 4.06 (s, 3H), 3.27 (s, 3H) 1.32 (s, 6H). Anal. Calcd for C$_{19}$H$_{18}$N$_2$O$_4$⅓CF$_3$COOH⅓H$_2$O: C, 61.78; H, 5.01; N, 7.33. Found: C, 61.64; H, 4.84; N, 7.51.

Example 1

10-Methoxy-2,2-dimethyl-5-phenyl-1,2,4,5-tetrahydro-6-oxa-1,4-diaza-chrysen-3-one (xi)

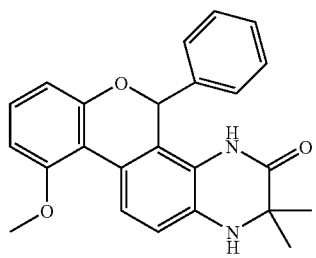

To a suspension of tetracyclic lactone x (19 mg, 0.059 mmol) in dry THF (1 mL) at −78° C. was added dropwise phenyl lithium (160 μL, 0.29 mmol) in cyclohexane/ether. The mixture was stirred at −78° C. for 30 min and then quenched with MeOH/H$_2$O (1 mL, 1:1) at −78° C. The mixture was warmed to room temperature and water was added (10 mL). After extraction (EtOAc, 3×10 mL), the combined extracts were washed with brine and dried over MgSO$_4$. The solvent was removed under reduced pressure to provide a yellow solid as the crude product. The crude was dissolved in dry CH$_2$Cl$_2$ (1 mL) and cooled to −78° C., BF$_3$.Et$_2$O (42 mg, 0.29 mmol) was added followed by Et$_3$SiH (34 mg, 0.29 mmol). The mixture was then warmed to room temperature. After stirring for 1.5 h, the mixture was cooled to 0° C. and saturated aqueous NaHCO$_3$ (3 mL) was added to quench the reaction. Water (10 mL) was added and the mixture was extracted by EtOAc (3×10 mL). The organic layers were combined, washed with brine and dried over MgSO$_4$. The solvent was removed under reduced pressure and the residue was purified by preparative thin layer chromatography to provide xi (5 mg, 28%) as a white solid. $^1$H NMR (acetone-d$_6$) δ 8.67 (br, 1H), 8.00 (d, J=9 Hz, 1H), 7.14 (m, 5H), 6.9 (t, J=9 Hz, 1H), 6.80 (d, J=9 Hz, 1H), 6.73 (s, 1H), 6.51 (d, J=9 Hz, 1H), 6.49 (d, J=9 Hz, 1H), 5.5 (br, 1H), 3.78 (s, 3H), 1.28 (s, 3H), 1.24 (s, 3H). HRMS (EI): m/z calcd for C$_{24}$H$_{22}$N$_2$O$_3$ 386.1630, found.

Example 2

10-Methoxy-2,2,4-trimethyl-5-phenyl-1,2,4,5-tetrahydro-6-oxa-1,4-diaza-chrysen-3-one (xii)

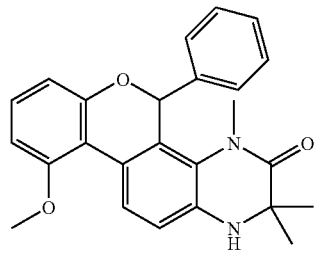

Compound xii was synthesized from x using a similar method used for the preparation of xi. Compound xii was obtained as a white solid (21%). $^1$H NMR (acetone-d$_6$) δ 8.61 (d, J=9 Hz, 1H), 7.32 (t, J=9 Hz, 1H), 7.25 (d, J=9 Hz, 1H), 6.95 (d, J=9 Hz, 1H), 6.87 (d, J=9 Hz, 1H), 6.04 (br, 1H), 3.99 (s, 3H), 3.19 (s, 3H), 1.25 (s, 6H). HRMS (EI): nz/z calcd for C$_{25}$H$_{24}$N$_2$O$_3$ 400.1787, found.

Example 3

5-Allyl-10-methoxy-2,2-dimethyl-1,2,4,5-tetrahydro-6-oxa-1,4-diaza-chrysen-3-one (xiii)

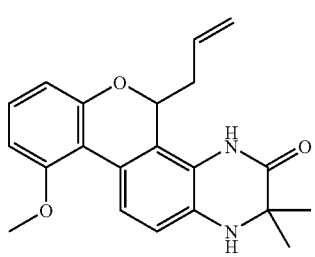

Lithium tri-t-butoxyaluminohydride (0.60 mL, 0.3 mmol) in diglyme was added dropwise to a solution of tetracyclic lactone ix (32 mg, 0.1 mmol) in dry THF (3 mL) at 0° C. The mixture was warmed to room temperature and stirred for 3 h. EtOH/H$_2$O (12 mL, 1:5) was added to quench the reaction. The mixture was diluted with EtOAc (10 mL) and extracted (EtOAc, 3×20 mL). The organic layers were combined, washed with brine and dried with MgSO$_4$. The solvent was removed under reduced pressure and the residue was re-dissolved in MeOH (3 mL), cooled to 0° C. and p-TSA (6 mg, ~20% weight) was added. The mixture was stirred for 30 min at 0° C. and then warmed to room temperature for 30 min. The mixture was cooled to 0° C. again and saturated aq NaHCO$_3$ (1 mL) was added. Water was added (10 mL) and the reaction was extracted with EtOAc (3×20 mL). The organic layers were combined, washed with brine and dried over MgSO$_4$. The solvent was removed under reduced pressure to provide a light yellow solid as the crude methyl acetal (xiv).

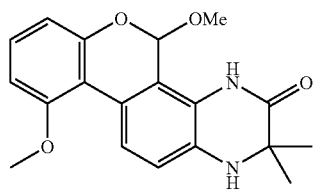

(xiv)

The resulting methyl acetal (xiv) was re-dissolved in CH$_2$Cl$_2$ (5 mL) and cooled to −5° C., then BF$_3$·Et$_2$O (50 μL, 0.39 mmol) was added. The greenish mixture was stirred at −5° C. for 30 min and allyl magnesium bromide (0.5 mL, 0.5 mmol) was added. The mixture was stirred for another 15 min at −5° C. and then quenched with saturated aqueous NH$_4$Cl (2 mL). The reaction was then warmed to room temperature and diluted with water (15 mL). After extraction with CH$_2$Cl$_2$ (3×20 mL), the organic layers were combined, washed with brine (2 mL) and dried over MgSO$_4$. The solvent was removed under reduced pressure and the residue was purified by preparative thin layer chromatography to provide xiii as a colorless solid (12 mg, 35% for the 3 steps). $^1$H NMR (acetone-d$_6$) δ 8.85 (br, 1H), 7.93 (d, J=9 Hz, 1H), 7.03 (t, J=9 Hz, 1H), 6.69 (d, J=9 Hz, 1H), 6.65 (d, J=9 Hz, 1H), 6.49, (d, J=9 Hz, 1H), 5.87 (s, 1H), 5.42 (br, 1H), 4.90 (m, 2H), 3.86 (s, 3H), 2.45 (m, 1H), 2.26 (m, 1H), 1.27 (s, 3H), 1.24 (s, 3H). HRMS (EI): m/z calcd for C$_{21}$H$_{22}$N$_2$O$_3$ 350.1630, found.

Example 4

5-Allyl-10-methoxy-2,2,4-trimethyl-1,2,4,5-tetrahydro-6-oxa-1,4-diaza-chrysen-3-one (xv)

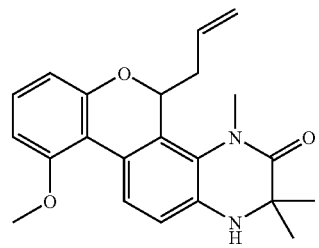

(xv)

To a solution of xiii (10 mg, 0.029 mmol) in CH$_3$CN (1 mL) was added cesium carbonate (14 mg, 0.043 mmol) and methyl iodide (3.5 mL, 0.57 mmol) and the mixture was stirred at room temperature for 12 hours. The mixture was diluted with water (10 mL) and extracted with EtOAc (3×10 mL). The organic extracts were combined, washed with brine and dried over MgSO$_4$. The solvent was removed under reduced pressure and the residue was purified by preparative thin layer chromatography to provide compounds xv (6.2 mg, 60%).

N-methylated product xv: $^1$H NMR (acetone-d$_6$) δ 8.08 (d, 1H, J=9 Hz), 7.07 (t, J=9 Hz, 1H), 6.8 (d, J=9 Hz, 1H), 6.68 (d, J=9 Hz, 1H), 6.52 (d, J=9 Hz, 1H), 5.77 (m, 1H), 5.62 (m, 1H), 5.42 (br, 1H), 4.90 (m, 2H), 3.88 (s, 3H), 3.36 (s, 3H), 2.52 (m, 1H), 2.24 (m, 1H), 1,24 (s, 3H), 1.12 (s, 3H); HRMS (EI): m/z calcd for C$_{22}$H$_{24}$N$_2$O$_3$ 364.1787, found.

The invention claimed is:
1. A compound having formula (I),

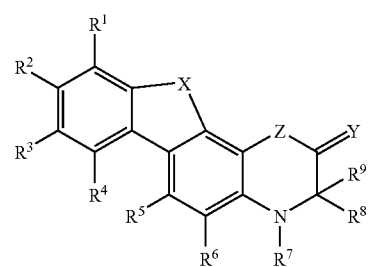

(I)

or a stereoisomer or pharmaceutically acceptable salt, thereof, wherein:
R$^1$ through R$^6$ are independently
(i) hydrogen, F, Cl, Br, I, NO$_2$, CN, OR$^{10}$, NR$^{10}$R$^{11}$, SR$^{10}$, COR$^{12}$, CO$_2$R$^{12}$, or CONR$^{10}$R$^{11}$; or
(ii) C$_{1-6}$alkyl, C$_{3-8}$cycloalkyl, C$_{2-6}$alkenyl, C$_{2-6}$alkynyl, aryl, or heteroaryl, each group of which is optionally substituted where valence allows by one or more groups, T$^1$, T$^2$ and/or T$^3$;
Y is O, S or NR$^{14}$;
Z is O, S, S(O), S(O)$_2$, or NR$^{15}$;
X is OCR$^{16}$R$^{17}$, SCR$^{16}$R$^7$, S(O)CR$^{16}$R$^{17}$, S(O)$_2$CR$^{16}$R$^{17}$ NR$^{14}$CR$^{16}$R$^{17}$, OC(O), SC(O), NR$^{18}$C(O), CR$^{16}$R$^{17}$O, CR$^{16}$R$^{17}$S, CR$^{16}$R$^{17}$S(O), CR$^{16}$R$^{17}$S(O)$_2$CR$^{16}$R$^{17}$NR$^{14}$, C(O)O, C(O)S, or C(O)NR$^{18}$;
R$^7$ and R$^{15}$ are independently hydrogen, C$_{1-6}$alkyl, C$_{3-8}$cycloalkyl, C$_{1-6}$haloalkyl, aryl, arylalkyl, heteroaryl, heteroarylalkyl, COR$^{12}$, CO$_2$R$^{12}$, SO$_2$R$^{12}$, S(O)R$^{12}$, or CONR$^{10}$R$^{11}$;
R$^8$ and R$^9$ are independently hydrogen, C$_{1-6}$alkyl, C$_{3-8}$cycloalkyl, C$_{2-6}$alkenyl, C$_{2-6}$alkynyl, allyl, arylalkyl, aryl, or heteroaryl, each group of which is optionally substituted where valence allows by one or more groups, T$^4$, T$^5$ and/or T$^6$;
R$^{10}$, R$^{11}$ and R$^{14}$ are independently
(i) hydrogen, C$_{1-6}$alkyl, C$_{3-8}$cycloalkyl, aryl, or heteroaryl, each group of which is optionally substituted where valence allows by, one or more groups, T$^7$, T$^8$ and/or T$^9$; or
(ii) COR$^{13}$, SO$_2$R$^{13}$, or S(O)R$^{13}$;
R$^{12}$ and R$^{13}$ are independently hydrogen, C$_{1-6}$alkyl, C$_{3-8}$cycloalkyl, substituted C$_{1-6}$alkyl, haloalkyl, aryl, or heteroaryl, $R^{16}$, $R^{17}$ and $R^{18}$ are independently hydrogen, $C_{1-6}$alkyl, $C_{3-8}$cycloalkyl, $C_{2-6}$alkenyl, $C_{2-6}$alkynyl, aryl, or heteroaryl, each group of which is optionally substituted where valence allows by one or more groups, $T^{10}$, $T^{11}$ and/or $T^{12}$;

$T^1$–$T^{12}$ are each independently (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, each group of which is optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT$^{13}$, —ST$^{13}$, —C(O)$_t$H, —C(O)$_t$T$^{13}$, —O—C(O)T$^{13}$, -T$^{20}$C(O)$_t$N(T$^{14}$)T$^{13}$, —SO$_3$H, —S(O)$_t$T$^{13}$, S(O)$_t$N(T$^{14}$)T$^{13}$, -T$^{15}$-NT$^{17}$T$^{18}$, -T$^{15}$-N(T$^{14}$)-T$^{16}$-NT$^{17}$T$^{18}$, -T$^{15}$-N(T$^{19}$)-T$^{18}$-T$^{13}$ and -T$^{15}$-N(T$^{19}$)-T$^{16}$-H; or (ii) halo, cyano, nitro, OH, oxo, —SH, OT$^{13}$, —ST$^{13}$, —C(O)$_t$H, —C(O)$_t$T$^{13}$, —O—C(O)T$^{13}$, -T$^{20}$C(O)$_t$N(T$^{14}$)T$^{13}$, —SO$_3$H, —S(O)$_t$T$^{13}$, S(O)$_t$N(T$^{14}$)T$^{13}$, -T$^{15}$-NT$^{17}$T$^{18}$, -T$^{15}$-N(T$^{14}$)-T$^{16}$-NT$^{17}$T$^{18}$, -T$^{15}$-N(T$^{19}$)-T$^{18}$-T$^{13}$, or T$^{15}$-N(T$^{19}$)-T$^{16}$-H;

t is 1 or 2;

$T^{13}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$T^{15}$ and $T^{16}$ are each independently a single bond, -T$^{20}$-S(O)$_t$-T$^{21}$-, -T$^{20}$-C(O)-T$^{21}$-, -T$^{20}$C(S)-T$^{21}$-, -T$^{20}$-O-T$^{21}$-, -T$^{20}$-S-T$^{21}$-, -T$^{20}$O—C(O)-T$^{21}$-, -T$^{20}$-C(O)$_t$T$^{21}$-, T$^{20}$-C(=NT$^{22}$)-T$^{21}$-or -T$^{20}$-C(O)—C(O)-T$^{21}$-;

$T^{14}$, $T^{17}$, $T^{18}$, $T^{19}$ and $T^{20}$ are independently alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT$^{23}$, —ST$^{23}$, —C(O)$_t$H, —C(O)$_t$T$^{23}$, —O—C(O)T$^{23}$, -T$^{20}$C(O)$_t$N(T$^{24}$)T$^{23}$, —SO$_3$H, —S(O)$_t$T$^{23}$, S(O)$_t$N(T$^{24}$)T$^{23}$, -T$^{25}$-NT$^{23}$T$^{24}$, -T$^{25}$-N(T$^{24}$)-T$^{26}$-NT$^{23}$T$^{24}$, -T$^{25}$-N(T$^{24}$)-T$^{26}$-T$^{23}$, and -T$^{25}$-N(T$^{24}$)-T$^{26}$-H; or $T^{21}$ and $T^{22}$ are each independently a single bond, alkylene, alkenylene, or alkynylene;

$T^{23}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$T^{24}$ is hydrogen, halo, cyano, OH, —SH, oxo, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —C(O)$_t$H or —SO$_3$H; and $T^{25}$ and $T^{26}$ are each independently a single bond, —S(O)$_t$—, —C(O)—, —C(S)—, —O—, —S—, —O—C(O)—, —C(O)$_t$—, —C(=NT$^{13}$),— or —C(O)—C(O)—.

2. A compound of claim 1, or a stereoisomer or pharmaceutically acceptable salt, thereof, wherein Z is NR$^{15}$.

3. A compound of claim 1, or a stereoisomer or pharmaceutically acceptable salt, thereof, wherein X is OCR$^{16}$R$^{17}$, SCR$^{16}$R$^{17}$, or NR$^{14}$CR$^{16}$R$^{17}$.

4. A compound of claim 1, or a stereoisomer or pharmaceutically acceptable salt, thereof, wherein R$^7$ is H or $C_{1-6}$alkyl.

5. A compound of claim 1, or a stereoisomer or pharmaceutically acceptable salt, thereof, wherein Y is O or S.

6. A compound having formula (II),

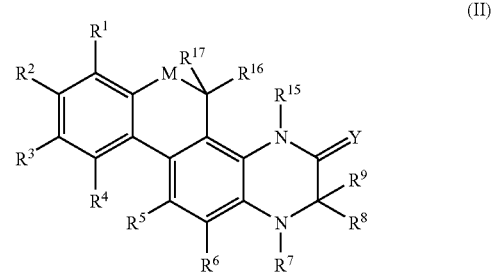

(II)

or a stereoisomer or pharmaceutically acceptable salt, thereof, wherein:

$R_1$ through $R^6$ are independently (i) hydrogen, F, Cl, Br, I, NO$_2$, CN, OR$^{10}$, NR$^{10}$OR$^{11}$, SR$^{10}$, COR$^{12}$, CO$_2$R$^{12}$, or CONR$^{10}$OR$^{11}$; or (ii) $C_{1-6}$alkyl, $C_{3-8}$cycloalkyl, $C_{2-6}$alkenyl, $C_{2-6}$alkynyl, aryl, or heteroaryl, each group of which is optionally substituted where valence allows by one or more groups, $T^1$, $T^2$ and/or $T^3$;

Y is O, S or NR$^{14}$;

M is O, S, S(O), or S(O)$_2$;

$R^7$ and $R^{15}$ are independently hydrogen, $C_{1-6}$alkyl, $C_{3-8}$cycloalkyl $C_{1-6}$haloalkyl, aryl, arylalkyl, heteroaryl, heteroarylalkyl, COR$^{12}$, CO$_2$R$^{12}$, SO$_2$R$^{12}$, S(O)R$^{12}$, or CONR$^{10}$R$^{11}$;

$R^8$ and $R^9$ are independently hydrogen, $C_{1-6}$alkyl, $C_{3-8}$cycloalkyl, $C_{2-6}$alkenyl, $C_{2-6}$alkynyl, allyl, arylalkyl, aryl, or heteroaryl, each group of which is optionally substituted where valence allows by one or more groups, $T^4$, $T^5$ and/or $T^6$;

$R^{10}$, $R^{11}$ and $R^{14}$ are independently (i) hydrogen, $C_{1-6}$alkyl, $C_{3-8}$cycloalkyl, aryl, or heteroaryl, each group of which is optionally substituted where valence allows, by one or more groups, $T^7$, $T^8$ and/or $T^9$; or (ii) COR$^{13}$, SO$_2$R$^{13}$, or S(O)R$^{13}$;

$R^{12}$ and $R^{13}$ are independently hydrogen, $C_{1-6}$alkyl, $C_{3-8}$cycloalkyl, substituted $C_{1-6}$alkyl, haloalkyl, aryl, or heteroaryl, $R^{16}$, $R^{17}$ and $R^{18}$ are independently hydrogen, $C_{1-6}$alkyl, $C_{3-8}$cycloalkyl, $C_{2-6}$alkenyl, $C_{2-6}$alkynyl, aryl, or heteroaryl, each group of which is optionally substituted where valence allows by one or more groups, $T^{10}$, $T^{11}$ and/or $T^{12}$;

$T^1$–$T^{12}$ are each independently (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, each group of which is optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{13}$, —$ST^{13}$, —$C(O)_tH$, —$C(O)T^{13}$, —O—$C(O)T^{13}$, -$T^{20}C(O)_tN(T^{14})T^{13}$, —$SO_3H$, —$S(O)_tT^{13}$, $S(O)_tN(T^{14})T^{13}$, -$T^{15}$-$NT^{17}T^{18}$, -$T^{15}$-$N(T^{14})$-$T^{16}$-$NT^{17}T^{18}$, -$T^{15}$-$N(T^{19})$-$T^{18}$-$T^{13}$, and $T^{15}$-$N(T^{19})$-$T^{16}$-H; or (ii) halo, cyano, nitro, OH, oxo, —SH, $OT^{13}$, —$ST^{13}$, —$C(O)_tH$, —$C(O)T^{13}$, —O—$C(O)T^{13}$, -$T^{20}C(O)_tN(T^{14})T^{13}$, —$SO_3H$, —$S(O)_tT^{13}$, $S(O)_tN(T^{14})T^{13}$, -$T^{15}$-$NT^{17}T^{18}$, -$T^{15}$-$N(T^{14})$-$T^{16}$-$NT^{17}T^{18}$, -$T^{15}$-$N(T^{19})$-$T^{18}$-$T^{13}$, or -$T^{15}$-$N(T^{19})$-$T^{16}$-H;

t is 1 or 2;

$T^{13}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$T^{15}$ and $T^{16}$ are each independently a single bond, -$T^{20}$-$S(O)_t$-$T^{21}$-, -$T^{20}$-C(O)-$T^{21}$-, -$T^{20}$-C(S)-$T^{21}$-, -$T^{20}$-O-$T^{21}$-, -$T^{20}$-S-$T^{21}$-, -$T^{20}$-O—C(O)-$T^{21}$-, -$T^{20}$-C(O)_t$T^{21}$-, -$T^{20}$-C(=$NT^{22}$)-$T^{21}$-, or -$T^{20}$-C(O)—C(O)-$T^{21}$-;

$T^{14}$, $T^{17}$, $T^{18}$, $T^{19}$ and $T^{20}$ are independently alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{23}$, —$ST^{23}$, —$C(O)_tH$, —$C(O)_tT^{23}$, —O—C(O)$T^{23}$, -$T^{20}C(O)_tN(T^{24})T^{23}$, —$SO_3H$, —$S(O)_tT^{23}$, $S(O)_tN(T^{24})T^{23}$, -$T^{25}$-$NT^{23}T^{24}$, -$T^{25}$-$N(T^{24})$-$T^{26}$-$NT^{23}T^{24}$, -$T^{25}$-$N(T^{24})$-$T^{26}$-$T^{23}$, and -$T^{25}$-$N(T^{24})$-$T^{26}$-H; or $T^{21}$ and $T^{22}$ are each independently a single bond, alkylene, alkenylene, or alkynylene;

$T^{23}$ is hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$T^{24}$ is hydrogen, halo, cyano, OH, —SH, oxo, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$C(O)_tH$, or —$SO_3H$; and $T^{25}$ and $T^{26}$ are each independently a single bond, —$S(O)_t$—, —C(O)—, —C(S)—, —O—, —S—, —O—C(O)—, —$C(O)_t$—, —C(=$NT^{13}$)—, or —C(O)—C(O)—.

7. A compound of claim 6, or a stereoisomer or pharmaceutically acceptable salt thereof, wherein M is O or S.

8. A compound of claim 7, or a stereoisomer or pharmaceutically acceptable salt, thereof, wherein Y is O or S.

9. A compound of claim 8, or a stereoisomer or pharmaceutically acceptable salt, thereof, wherein $R^1$–$R^6$ are chosen independently from hydrogen, F, Cl, Br, I, $NO_2$, CN, $OR^{10}$, $NR^{10}R^{11}$, $SR^{10}$, and optionally substituted $C_{1-6}$alkyl.

10. A compound of claim 9, or a stereoisomer or pharmaceutically acceptable salt, thereof, wherein $R^7$ and $R^{15}$ are independently H or $C_{1-6}$alkyl.

11. A compound of claim 10, or a stereoisomer or pharmaceutically acceptable salt, thereof, wherein $R^8$, $R^9$, and $R^{17}$ are independently chosen from H and $C_{1-6}$alkyl.

12. A compound of claim 11 having formula (III), (III)

or a stereoisomer or pharmaceutically acceptable salt, thereof, wherein:

$R^4$ is $OR^{10}$ or $SR^{10}$; and $R^{10}$ is $C_{1-6}$alkyl optionally substituted where valence allows, by one or more groups, $T^7$, $T^8$, and/or $T^9$.

13. A compound of claim 12, or a stereoisomer or pharmaceutically acceptable salt, thereof, wherein:

$R^4$ is $OC_{1-6}$alkyl;

$R^8$ and $R^9$ are independently $C_{1-6}$alkyl.

14. A compound of claim 12, or a stereoisomer or pharmaceutically acceptable salt, thereof, wherein $R^{16}$ is unsubstituted allyl.

15. A compound of claim 12, or a stereoisomer or pharmaceutically acceptable salt, thereof, wherein $R^{16}$ is unsubstituted aryl.

16. A compound having formula (IV), (IV)

or a stereoisomer or pharmaceutically acceptable salt, thereof, wherein:

$R^4$ is $OR^{10}$ or $SR^{10}$;

$R^7$ is hydrogen, $C_{1-6}$alkyl, or $C_{1-6}$haloalkyl;

$R^8$ and $R^9$ are independently chosen from H and $C_{1-6}$alkyl;

$R^{10}$ is $C_{1-6}$alkyl optionally substituted where valence allows, by one or more groups, $T^7$, $T^8$, and/or $T^9$;

Y is O, S, or $NR^{14}$;

Z is O, S, S(O), $S(O)_2$, or $NR^{15}$;

$R^{13}$ is hydrogen, $C_{1-6}$alkyl, $C_{3-8}$cycloalkyl, substituted $C_{1-6}$alkyl, haloalkyl, aryl, or heteroaryl;

$R^{14}$ is hydrogen, $C_{1-6}$alkyl, $C_{3-8}$cycloalkyl, or $C_{1-6}$alkyl optionally substituted by one or more groups, $T^7$, $T^8$ and/or $T^9$;

$R^{15}$ is hydrogen, $C_{1-6}$alkyl, $C_{3-8}$cycloalkyl, $C_{1-6}$haloalkyl, arylalkyl, or heteroalkyl; and $R^{16}$ is hydrogen, $C_{1-6}$alkyl, $C_{3-8}$cycloalkyl, $C_{2-6}$alkenyl, $C_{2-6}$alkynyl, aryl, or heteroaryl, each group of which is optionally substituted where valence allows by one or more groups, $T^{10}$, $T^{11}$, and/or $T^{12}$.

17. A compound of claim 16, or a stereoisomer or pharmaceutically acceptable salt, thereof, wherein:

$R^4$ is $OC_{1-6}$alkyl;

$R^7$ is hydrogen;

$R^8$ and $R^9$ are independently $C_{1-6}$alkyl;

Z is $NR^{15}$;

Y is O;

$R^{14}$ and $R^{15}$ are independently H or $C_{1-6}$alkyl; and $R^{16}$ is allyl or aryl, each group of which is optionally substituted by one or more groups, $T^{10}$, $T^{11}$, and/or $T^{12}$.

18. A compound selected from:

(i)

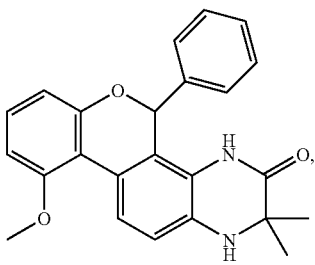

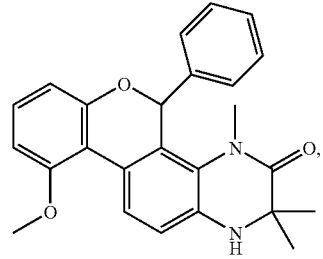

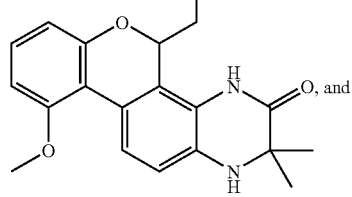

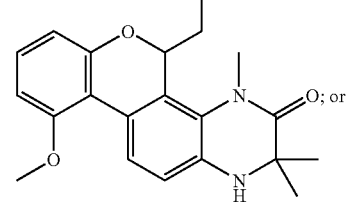

(ii) a stereoisomer or pharmaceutically acceptable salt of (i), thereof.

* * * * *

UNITED STATES PATENT AND TRADEMARK OFFICE
CERTIFICATE OF CORRECTION

PATENT NO. : 7,235,662 B2 Page 1 of 1
APPLICATION NO. : 10/865444
DATED : June 26, 2007
INVENTOR(S) : Sara Sabine Hadida-Ruah et al.

It is certified that error appears in the above-identified patent and that said Letters Patent is hereby corrected as shown below:

In the Claims:

Col. 47, line 36 Claim 1, change "-$T^{20}$O-C(O)-$T^{21}$-" to -- -$T^{20}$-O-C(O)-$T^{21}$- --.

Col. 47, line 37 Claim 1, change "$T^{20}$-C(=$NT^{22}$)-$T^{21}$-or" to -- -$T^{20}$-C(=$NT^{22}$)-$T^{21}$-,  or --.

Col. 48, line 33 Claim 6, change "$NR^{10}OR^{11}$" to -- $NR^{10}R^{11}$ --.

Col. 48, line 34 Claim 6, change "$CONR^{10}OR^{11}$" to -- $CONR^{10}R^{11}$ --.

Signed and Sealed this

Twenty-second Day of July, 2008

JON W. DUDAS
*Director of the United States Patent and Trademark Office*